US010517860B2

(12) United States Patent
Parkinson

(10) Patent No.: US 10,517,860 B2
(45) Date of Patent: *Dec. 31, 2019

(54) COMBINATION OF PIMAVANSERIN AND CYTOCHROME P450 MODULATORS

(71) Applicant: ACADIA Pharmaceuticals Inc., San Diego, CA (US)

(72) Inventor: Andrew Parkinson, Shawnee, KS (US)

(73) Assignee: ACADIA Pharmaceuticals Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/379,169

(22) Filed: Apr. 9, 2019

(65) Prior Publication Data

US 2019/0231767 A1 Aug. 1, 2019

Related U.S. Application Data

(63) Continuation of application No. 16/087,604, filed as application No. PCT/US2017/023795 on Mar. 23, 2017.

(60) Provisional application No. 62/313,674, filed on Mar. 25, 2016, provisional application No. 62/367,565, filed on Jul. 27, 2016.

(30) Foreign Application Priority Data

Apr. 4, 2016 (SE) ..................................... 1630068

(51) Int. Cl.
| | | |
|---|---|---|
| A61K 31/4468 | (2006.01) | |
| A61K 31/496 | (2006.01) | |
| A61K 31/7048 | (2006.01) | |
| A61K 9/00 | (2006.01) | |
| A61K 45/06 | (2006.01) | |
| A61P 25/28 | (2006.01) | |
| A61P 25/18 | (2006.01) | |
| A61P 25/24 | (2006.01) | |
| A61P 25/16 | (2006.01) | |

(52) U.S. Cl.
CPC ............ *A61K 31/4468* (2013.01); *A61K 9/00* (2013.01); *A61K 45/06* (2013.01); *A61P 25/16* (2018.01); *A61P 25/18* (2018.01); *A61P 25/24* (2018.01); *A61P 25/28* (2018.01); *A61K 31/496* (2013.01); *A61K 31/7048* (2013.01)

(58) Field of Classification Search
CPC ............ A61K 31/4468; A61K 31/496; A61K 31/7048; A61K 9/00; A61K 45/06; A61P 25/16; A61P 25/18; A61P 25/28; A61P 25/24

See application file for complete search history.

(56) References Cited

U.S. PATENT DOCUMENTS

| | | |
|---|---|---|
| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Igleasias et al. |
| 4,853,394 A | 8/1989 | King |
| 5,025,013 A | 6/1991 | Barreau |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda |
| 5,707,798 A | 1/1998 | Brann |
| 5,795,894 A | 8/1998 | Shue |
| 5,837,730 A | 11/1998 | Javitt |
| 5,869,488 A | 2/1999 | Shue |
| 5,877,173 A | 3/1999 | Olney |
| 5,912,132 A | 6/1999 | Brann |
| 5,955,281 A | 9/1999 | Brann |
| 6,107,324 A | 8/2000 | Behan |
| 6,140,509 A | 10/2000 | Behan |
| 6,150,393 A | 11/2000 | Behan |
| 6,358,698 B1 | 3/2002 | Weiner et al. |
| 6,451,343 B1 | 9/2002 | Glinecke et al. |
| 6,479,480 B1 | 11/2002 | Moyes |
| 6,486,153 B1 | 11/2002 | Castro Pineiro |
| 6,670,137 B2 | 12/2003 | VanMechelen et al. |
| 6,756,393 B2 | 6/2004 | Andersson et al. |

(Continued)

FOREIGN PATENT DOCUMENTS

| | | |
|---|---|---|
| CA | 984843 A | 3/1976 |
| CN | 104844502 A | 8/2015 |

(Continued)

OTHER PUBLICATIONS

U.S. Appl. No. 09/800,096, Azacyclic compounds, filed Mar. 6, 2001, Issued, U.S. Pat. No. 6,815,458.

U.S. Appl. No. 10/409,782, Azacyclic compounds, filed Apr. 7, 2003, Issued, U.S. Pat. No. 6,756,393.

U.S. Appl. No. 13/053,079, Methods of treatment using selective 5-HT2A inverse agonists, filed Mar. 21, 2011, Issued, U.S. Pat. No. 9,765,053.

U.S. Appl. No. 14/628,156, Azacyclic compounds, filed Feb. 20, 2015, Issued, U.S. Pat. No. 9,296,694.

(Continued)

*Primary Examiner* — Sarah Pihonak

(74) *Attorney, Agent, or Firm* — Goodwin Procter LLP

(57) ABSTRACT

A method for treating a disease or disorder in a patient who is currently taking a cytochrome P450 inhibitor comprising administering to the patient a dose of pimavanserin or a pharmaceutical acceptable salt thereof, wherein the dose is at least 20% lower than a dose of pimavanserin or a pharmaceutical acceptable salt thereof that would otherwise have been recommended to the patient if the patient were not currently taking the cytochrome P450 inhibitor.

5 Claims, No Drawings

(56) References Cited

U.S. PATENT DOCUMENTS

| | | |
|---|---|---|
| 6,815,458 B2 | 11/2004 | Andersson et al. |
| 6,911,452 B2 | 6/2005 | Schlienger |
| 7,022,698 B2 | 4/2006 | Hamied et al. |
| 7,041,667 B1 | 5/2006 | Armour et al. |
| 7,115,634 B2 | 10/2006 | Thurieau et al. |
| 7,217,719 B2 | 5/2007 | Schlienger |
| 7,253,186 B2 | 8/2007 | Andersson et al. |
| 7,351,707 B2 | 4/2008 | Schlienger |
| 7,393,861 B2 | 7/2008 | Thurieau et al. |
| 7,476,682 B2 | 1/2009 | Andersson et al. |
| 7,538,222 B2 | 5/2009 | Andersson et al. |
| 7,601,740 B2 | 10/2009 | Andersson et al. |
| 7,659,285 B2 | 2/2010 | Weiner et al. |
| 7,713,995 B2 | 5/2010 | Weiner et al. |
| 7,732,462 B2 | 6/2010 | Weiner et al. |
| 7,732,615 B2 | 6/2010 | Thygesen et al. |
| 7,790,899 B2 | 9/2010 | Tolf et al. |
| 7,816,383 B1 | 10/2010 | Bradford et al. |
| 7,820,695 B2 | 10/2010 | Weiner et al. |
| 7,858,789 B2 | 12/2010 | Thurieau et al. |
| 7,863,296 B2 | 1/2011 | Weiner et al. |
| 7,868,176 B2 | 1/2011 | Thygesen et al. |
| 7,875,632 B2 | 1/2011 | Weiner et al. |
| 7,923,564 B2 | 4/2011 | Thygesen et al. |
| 7,994,193 B2 | 8/2011 | Weiner et al. |
| 8,008,323 B2 | 8/2011 | Weiner et al. |
| 8,110,574 B2 | 2/2012 | Thurieau et al. |
| 8,227,487 B2 | 7/2012 | Weiner et al. |
| 8,236,960 B2 | 8/2012 | Thygesen et al. |
| 8,377,959 B2 | 2/2013 | Weiner et al. |
| 8,618,130 B2 | 12/2013 | Weiner et al. |
| 8,921,393 B2 | 12/2014 | Weiner et al. |
| 9,050,343 B2 | 6/2015 | Peters et al. |
| 9,211,289 B2 | 12/2015 | Weiner et al. |
| 9,296,694 B2 | 3/2016 | Andersson et al. |
| 9,446,037 B2 | 9/2016 | Mills et al. |
| 9,486,453 B2 | 11/2016 | Javitt |
| 9,566,271 B2 | 2/2017 | Weiner et al. |
| 9,757,366 B2 | 9/2017 | Mills et al. |
| 9,765,053 B2 | 9/2017 | Andersson et al. |
| 10,028,944 B2 | 7/2018 | Weiner et al. |
| 2002/0156068 A1 | 10/2002 | Behan |
| 2002/0165225 A1 | 11/2002 | Kankan et al. |
| 2004/0006081 A1 | 1/2004 | Burrows |
| 2004/0106600 A1 | 6/2004 | Andersson et al. |
| 2004/0213816 A1 | 10/2004 | Weiner et al. |
| 2004/0229908 A1* | 11/2004 | Nelson .................. A61K 31/355 514/313 |
| 2005/0014757 A1 | 1/2005 | Andersson et al. |
| 2005/0148018 A1 | 7/2005 | Weiner et al. |
| 2005/0244862 A1 | 11/2005 | Brann |
| 2005/0256108 A1 | 11/2005 | Schlienger |
| 2005/0261278 A1 | 11/2005 | Weiner et al. |
| 2005/0261340 A1 | 11/2005 | Weiner et al. |
| 2005/0288328 A1 | 12/2005 | Weiner et al. |
| 2006/0094758 A1 | 5/2006 | Andersson et al. |
| 2006/0106063 A1 | 5/2006 | Thhygesen et al. |
| 2006/0111399 A1 | 5/2006 | Thhygesen et al. |
| 2006/0194778 A1 | 8/2006 | Andersson et al. |
| 2006/0194834 A1 | 8/2006 | Andersson et al. |
| 2006/0199794 A1 | 9/2006 | Schlienger |
| 2006/0199818 A1 | 9/2006 | Andersson et al. |
| 2006/0199842 A1 | 9/2006 | Weiner et al. |
| 2006/0204486 A1 | 9/2006 | Pyke et al. |
| 2006/0205710 A1 | 9/2006 | Schlienger |
| 2006/0205722 A1 | 9/2006 | Andersson et al. |
| 2006/0205780 A1 | 9/2006 | Thygesen et al. |
| 2006/0205781 A1 | 9/2006 | Thygesen et al. |
| 2006/0264465 A1 | 11/2006 | Weiner et al. |
| 2006/0264466 A1 | 11/2006 | Weiner et al. |
| 2006/0286610 A1 | 12/2006 | Brann |
| 2006/0292606 A1 | 12/2006 | Brann |
| 2007/0260064 A1 | 11/2007 | Tolf et al. |
| 2007/0264330 A1 | 11/2007 | Ragnar-Tolf |
| 2008/0051429 A1 | 2/2008 | Van Kammen et al. |
| 2008/0280886 A1 | 11/2008 | Gant et al. |
| 2009/0053329 A1 | 2/2009 | Peters et al. |
| 2009/0082342 A1 | 3/2009 | Uldam et al. |
| 2009/0082388 A1 | 3/2009 | Hacksell |
| 2009/0186921 A1 | 7/2009 | Andersson et al. |
| 2014/0018348 A1 | 1/2014 | Javitt |
| 2014/0162942 A1* | 6/2014 | Ghosal .................. A61K 38/07 514/4.3 |
| 2014/0221395 A1 | 8/2014 | Dhanoa |
| 2014/0329903 A1 | 11/2014 | Burstein et al. |
| 2014/0349976 A1 | 11/2014 | Hacksell et al. |
| 2015/0231126 A1 | 8/2015 | Peters |
| 2016/0237036 A1 | 8/2016 | Andersson et al. |
| 2018/0037549 A1 | 2/2018 | Biljan |
| 2019/0030015 A1 | 1/2019 | Weiner et al. |
| 2019/0047955 A1 | 2/2019 | Carlos et al. |

FOREIGN PATENT DOCUMENTS

| | | |
|---|---|---|
| CN | 104961672 A | 10/2015 |
| CN | 105111135 A | 12/2015 |
| CN | 105153016 A | 12/2015 |
| CN | 105418460 A | 3/2016 |
| CN | 105481757 A | 4/2016 |
| CN | 105820110 A | 8/2016 |
| CN | 106543072 A | 3/2017 |
| EP | 0005318 B1 | 11/1979 |
| EP | 0061333 B1 | 9/1982 |
| EP | 0260070 B1 | 3/1988 |
| EP | 0379441 A1 | 7/1990 |
| EP | 0548015 B1 | 6/1993 |
| EP | 0625507 B1 | 11/1994 |
| EP | 1576985 A1 | 9/2005 |
| HU | 157325 | 3/1998 |
| JP | 51052176 | 5/1976 |
| JP | 52085174 A | 7/1977 |
| WO | WO-94/27967 A1 | 12/1994 |
| WO | WO-97/08166 A1 | 3/1997 |
| WO | WO-97/11940 A1 | 4/1997 |
| WO | WO-97/38665 A2 | 10/1997 |
| WO | WO-97/38984 A1 | 10/1997 |
| WO | WO-98/11128 A1 | 3/1998 |
| WO | WO-9817646 A1 | 4/1998 |
| WO | WO-98/44921 A1 | 10/1998 |
| WO | WO-98/50534 A1 | 11/1998 |
| WO | WO-99/52927 A1 | 10/1999 |
| WO | WO-00/23076 A1 | 4/2000 |
| WO | WO-00/56335 A1 | 9/2000 |
| WO | WO-00/59497 A1 | 10/2000 |
| WO | WO-00/69810 A1 | 11/2000 |
| WO | WO-01/44191 A1 | 6/2001 |
| WO | WO-01/66521 A1 | 9/2001 |
| WO | WO-01/87839 A1 | 11/2001 |
| WO | WO-2001089498 A2 | 11/2001 |
| WO | WO-02/24649 A1 | 3/2002 |
| WO | WO-2002038142 A2 | 5/2002 |
| WO | WO-02/076464 A1 | 10/2002 |
| WO | WO-02/079186 A2 | 10/2002 |
| WO | WO-03/057698 A2 | 7/2003 |
| WO | WO-03/062206 A2 | 7/2003 |
| WO | WO-03/070246 A1 | 8/2003 |
| WO | WO-03/086400 A1 | 10/2003 |
| WO | WO-04/000808 A2 | 12/2003 |
| WO | WO-04/039322 A2 | 5/2004 |
| WO | WO-04/064753 A2 | 8/2004 |
| WO | WO-2004064738 A2 | 8/2004 |
| WO | WO-05/053796 A1 | 6/2005 |
| WO | WO-05/063254 A2 | 7/2005 |
| WO | WO-05/112927 A1 | 12/2005 |
| WO | WO-06/036874 A1 | 4/2006 |
| WO | WO-2006037043 A1 | 4/2006 |
| WO | WO-06/104826 A2 | 10/2006 |
| WO | WO-2007/124136 A1 | 11/2007 |
| WO | WO-2007133802 A2 | 11/2007 |
| WO | WO-2008/116024 A2 | 9/2008 |
| WO | WO-2008/144326 A2 | 11/2008 |
| WO | WO-2008141057 A1 | 11/2008 |
| WO | WO-2008144665 A1 | 11/2008 |
| WO | WO-2009035473 A2 | 3/2009 |

(56) References Cited

FOREIGN PATENT DOCUMENTS

| WO | WO-2009039460 A2 | 3/2009 |
|---|---|---|
| WO | WO-2009039461 A2 | 3/2009 |
| WO | WO-2010/111353 A1 | 9/2010 |
| WO | WO-2011085216 A2 | 7/2011 |
| WO | WO-2014085362 A1 | 6/2014 |
| WO | WO-2016201373 A1 | 12/2016 |
| WO | WO-2017011767 A2 | 1/2017 |
| WO | WO-2017015272 A1 | 1/2017 |
| WO | WO-2017/165635 A1 | 9/2017 |
| WO | WO-2017/172757 A1 | 10/2017 |
| WO | WO-2018/118626 A1 | 6/2018 |
| WO | WO-2018/200977 A1 | 11/2018 |
| WO | WO-2019/046167 A1 | 3/2019 |

OTHER PUBLICATIONS

U.S. Appl. No. 10/759,561, Selective serotonin 2A/2C receptor inverse agonists as therapeutics for neurodegenerative diseases, filed Jan. 15, 2004, Issued, U.S. Pat. No. 7,601,740.
U.S. Appl. No. 11/416,527, Selective Serotonin 2A/2C Receptor Inverse Agonists as Therapeutics for Neurodegenerative Diseases, filed May 3, 2006, Issued, U.S. Pat. No. 7,732,462.
U.S. Appl. No. 11/416,855, Selective serotonin 2A/2C receptor inverse agonists as therapeutics for neurodegenerative diseases, filed May 3, 2006, Issued, U.S. Pat. No. 7,659,285.
U.S. Appl. No. 11/16,594, Selective serotonin 2A/2C receptor inverse agonists as therapeutics for neurodegenerative diseases, filed May 3, 2006, Issued, U.S. Pat. No. 7,713,995.
U.S. Appl. No. 12/759,662, Selective serotonin 2A/2C receptor inverse agonists as therapeutics for neurodegenerative diseases, filed Apr. 13, 2010, Issued, U.S. Pat. No. 7,994,193.
U.S. Appl. No. 12/759,664, Selective serotonin 2A/2C receptor inverse agonists as therapeutics for neurodegenerative diseases, filed Apr. 13, 2010, Issued, U.S. Pat. No. 8,008,323.
U.S. Appl. No. 13/169,893, Selective serotonin 2A/2C receptor inverse agonists as therapeutics for neurodegenerative diseases, filed Jun. 27, 2011, Issued, U.S. Pat. No. 8,227,487.
U.S. Appl. No. 13/539,011, Selective serotonin 2A/2C receptor inverse agonists as therapeutics for neurodegenerative diseases, filed Jun. 29, 2012, Issued, U.S. Pat. No. 8,377,959.
U.S. Appl. No. 13/750,778, Selective serotonin 2A/2C receptor inverse agonists as therapeutics for neurodegenerative diseases, filed Jan. 25, 2013, Issued, U.S. Pat. No. 8,618,130.
U.S. Appl. No. 14/086,838, Selective serotonin 2A/2C receptor inverse agonists as therapeutics for neurodegenerative diseases, filed Nov. 21, 2013, Issued, U.S. Pat. No. 8,921,393.
U.S. Appl. No. 14/537,793, Selective serotonin 2A/2C receptor inverse agonists as therapeutics for neurodegenerative diseases, filed Nov. 10, 2014, Issued, U.S. Pat. No. 9,211,289.
U.S. Appl. No. 14/935,246, Selective serotonin 2A/2C receptor inverse agonists as therapeutics for neurodegenerative diseases, filed Nov. 6, 2015, Issued, U.S. Pat. No. 9,566,271.
U.S. Appl. No. 15/397,582, Selective serotonin 2A/2C receptor inverse agonists as therapeutics for neurodegenerative diseases, filed Jan. 3, 2017, Issued, U.S. Pat. No. 10,028,944.
U.S. Appl. No. 16/019,485, Selective serotonin 2A/2C receptor inverse agonists as therapeutics for neurodegenerative diseases, filed Jun. 26, 2018, Pending, 20190030015.
U.S. Appl. No. 10/850,819, Selective serotonin receptor inverse agonists as therapeutics for disease, filed May 21, 2004, Issued, U.S. Pat. No. 7,820,695.
U.S. Appl. No. 11/134,769, Selective serotonin receptor inverse agonists as therapeutics for disease, filed May 20, 2005, Issued, U.S. Pat. No. 7,863,296.
U.S. Appl. No. 12/378,385, Selective serotonin receptor inverse agonists as therapeutics for disease, filed Feb. 11, 2009, Issued, U.S. Pat. No. 7,875,632.
U.S. Appl. No. 11/235,558, N-(4-fluorobenzyl)-N-(1-methylpiperidin-4-yl)-N'-(4-(2-methylpropyloxy)phenylmethyl)carbamide and its tartrate salt and crystalline forms, filed Sep. 26, 2005, Issued, U.S. Pat. No. 7,732,615.
U.S. Appl. No. 11/235,381, Salts of N-(4-fluorobenzyl)-N-(1-methylpiperidin-4-yl)-N'-(4-(2-methylpropyloxy)phenylmethyl)carbamide and their preparation, filed Sep. 26, 2005, Issued, U.S. Pat. No. 7,868,176.
U.S. Appl. No. 12/795,547, Synthesis of N-(4-fluorobenzyl)-N-(1-methylpiperidin-4-yl)-N'-(4-(2-methylpropyloxy)phenylmethyl)carbamide and its tartrate salt and crystalline forms, filed Jun. 7, 2010, Issued, U.S. Pat. No. 7,923,564.
U.S. Appl. No. 13/081,427, Synthesis of N-(4-fluorobenzyl)-N-(1-methylpiperidin-4-yl)-N'-(4-(2-methylpropyloxy)phenylmethyl)carbamide and its tartrate salt and crystalline forms, filed Apr. 6, 2011, Issued, U.S. Pat. No. 8,236,960.
U.S. Appl. No. 11/749,115, Synthesis of N-(4-fluorobenzyl)-N-(1-methylpiperidin-4-yl)-N'-(4-(2-methylpropyloxy)phenylmethyl)carbamide and its tartrate salt and crystalline forms, filed May 15, 2007, Issued, U.S. Pat. No. 7,790,899.
U.S. Appl. No. 13/754,769, Combination of pimavanserin and risperidone for the treatment of psychosis, filed Jan. 30, 2013, Issued, U.S. Pat. No. 9,050,343.
U.S. Appl. No. 14/647,438, Methods for the treatment of Parkinson's disease psychosis using pimavanserin, filed May 26, 2015, Issued, U.S. Pat. No. 9,446,037.
U.S. Appl. No. 15/246,412, Methods for the treatment of Parkinson's disease psychosis using pimavanserin, Issued, U.S. Pat. No. 9,757,366.
U.S. Appl. No. 15/744,636, Methods for preparing N-(4-fluorobenzyl)-N-(1-methylpiperidin-4-yl)-N'-(4-(2-methylpropyloxy)phenylmethyl)carbamide and its tartrate salt and polymorphic form, filed Jan. 12, 2018, Pending 20190047955.
U.S. Appl. No. 16/089,316, 5-HT2A serotonin receptor inverse agonists or antagonists for use in reducing amyloid-beta peptides and accumulation of amyloid plaques, filed Sep. 27, 2018, Pending, N/A.
U.S. Appl. No. 16/087,604, Combination of pimavanserin and cytochrome p450 modulators, filed Sep. 21, 2018, Pending, N/A.
U.S. Appl. No. 16/363,378, Formulations of pimavanserin, filed Mar. 25, 2019, Pending, N/A.
Swedish Search Report for Patent Application No. 1730232-4 dated Mar. 28, 2018 (10 pages).
"ACP-103," *Drugs of the Future, Prous Science* (2006) vol. 31, No. 11, pp. 939-943.
"FDA Briefing Document Psychopharmacologic Drugs Advisory Committee (PDAC) Meeting," Mar. 29, 2016. Retrieved from the Internet (URL): https://www.fda.gov/downloads/AdvisoryCommittees/CommitteesMeetingMaterials/Drugs/PsychopharmacologicDrugsAdvisoryCommittee/UCM492452.pdf (107 pages).
"Meeting of the Psychopharmacologic Drugs Advisory Committee (PDAC)," Silver Spring (MD): FDA Center for Drug Evaluation and Research, FDA White Oak Campus, Mar. 29, 2016, Retrieved from the Internet (URL): https://www.fda.gov/downloads/AdvisoryCommittees/CommitteesMeetingMaterials/Drugs/PsychopharmacologicDrugsAdvisoryCommittee/UCM502050.pdf (355 pages).
"NUPLAZID™ (pimavanserin) ACADIA Pharmaceuticals Inc. Mar. 29, 2016 Psychopharmacologic Drugs Advisory Committee of the Food and Drug Administration," Retrieved from the Internet (URL): https://www.fda.gov/downloads/AdvisoryCommittees/CommitteesMeetingMaterials/Drugs/PsychopharmacologicDrugsAdvisoryCommittee/UCM493998.pdf (110 pages).
"Pimavanserin (Nuplazid) for parkinson's disease psychosis," Medical Letter on Drugs and Therapeutics, New Rochelle, NY, US (Jun. 2016) vol. 58, pp. 74-75.
"Summary Minutes Meeting of the Psychopharmacologic Drugs Advisory Committee," Silver Spring (MD): FDA Center for Drug Evaluation and Research, FDA White Oak Campus, Mar. 29, 2016. Retrieved from the Internet (URL): https://www.fda.gov/downloads/AdvisoryCommittees/CommitteesMeetingMaterials/Drugs/PsychopharmacologicDrugsAdvisoryCommittee/UCM502046.pdf (5 pages).
Aarsland et al., "Decreased burden among caregivers of patients with Parkinson's disease psychosis (PDP) treated with pimavanserin,

(56) References Cited

OTHER PUBLICATIONS a selective 5-HT2A inverse agonist," (Meeting Abstract) *Neurology* (2015) vol. 84, No. 14, Suppl P6.044.
Abbas et al., "Pimavanserin tartrate: a 5-HT2A inverse agonist with potential for treating various neuropsychiatric disorders," *Expert Opinion on Pharmacotherapy* (2008) vol. 9, No. 18, pp. 3251-3259.
Acadia Pharmaceuticals, "FDA approves Acadia Pharmaceuticals' NUPLAZID™ (pimavanserin)—The First Drug Approved for the Treatment of Hallucinations and Delusions Associated with Parkinson's Disease Psychosis," Press Release, San Diego (CA) Apr. 29, 2016. Retrieved from the Internet (URL): http://ir.acadia-pharm.com/phoenix.zhtml?c=125180&p=irol-newsArticle&ID=2163521 (6 pages).
Adam, et al., "Effects of repeated ritanserin on middle-aged poor sleepers," *Psychopharmacology* (1989) 99:219-221.
Administrative and Correspondence Documents, Application Number: 207318Orig1s000, Center for Drug Evaluation and Research, Approval Date Apr. 29, 2016 [available online Jun. 3, 2016]. Retrieved from the Internet (URL): https://www.accessdata.fda.gov/drugsatfda_docs/nda/2016/207318Orig1s000AdminCorres.pdf (136 pages).
Akin, et al., "Decreased serotonin 5-HT 2A receptor-stimulated phosphoinositide signaling in fibroblasts from melancholic depressed patients," *Neuropsychopharmacology* (2004) 29:2081-2087.
Antunes, et al., "The novel object recognition memory: neurobiology, test procedure, and its modifications," *Cogn. Process* (2012) 13:93-110.
Approval Package for: Application Number: 207318Orig1s000, Center for Drug Evaluation and Research, Approval Date Apr. 28, 2016. [available online Jun. 3, 2016]. Retrieved from the Internet (URL): https://www.accessdata.fda.gov/drugsatfda_docs/nda/2016/207318Orig1s000Approv.pdf (10 pages).
Bakshi, et al., "Clozapine antagonizes phencyclidine-induced deficits in sensorimotor gating of the startle response," *The Journal of Pharmacology and Experimental Therapeutics* (1994) 271(2):787-794.
Bennett, et al., "Suppression of dyskinesias in advanced Parkinson's disease. II. Increasing daily clozapine doses suppress dyskinesias and improve parkinsonism symptoms," *Neurology* (1993) 43:1551-1554.
Biagi, et al., "1,2,3-Triazoles: Structural changes on two effective inhibitors of the prostaglandin synthesis in vitro," *Farmaco Ed. Sci.* (1988) 43:597-611.
Bibbiani, et al., "Serotonin 5-HT1A agonist improves motor complications in rodent and primate parkinsonian models," *Neurology* (2001) 57:1829-1834.
Blakley, et al., "Bidirectional changes in ethanol consumption in rats with site-specific antisense down-regulation of 5-hydroxytryptamine2A receptors in brain," *The Journal of Pharmacology and Experimental Therapeutics* (2001) 299(1):277-289.
Blier, et al., "Potential mechanisms of action of atypical antipsychotic medications in treatment-resistant depression and anxiety," *J. Clin. Psychiatry* (2005) 66(suppl 8):30-40.
Blier, et al., "Putative mechanisms of action of antidepressant drugs in affective and anxiety disorders and pain," *Journal of Psychiatry & Neuroscience* (2001) 26(1):37-43.
Bogolubsky et al., "Bis(2,2,2-trifluoroethyl) carbonate as a condensing agent in one-pot parallel synthesis of unsymmetrical aliphatic ureas," (2014), pp. S1-S67. Retrieved from URL: http://pubs.acs.org/doi/suppl/1 0.102 1/co500025f/supl_file co500025f_si_001.pdf.
Bogolubsky et al., "Bis(2,2,2-trifluoroethyl) carbonate as a condensing agent in one-pot parallel synthesis of unsymmetrical aliphatic ureas," *ACS Combinatorial Science* (2014) vol. 16, Issue 6, pp. 303-308.
Bond et al., "Physiological effects of inverse agonists in transgenic mice with myocardial overexpression of the beta-adrenoceptor," *Nature* (1995) 374:272-276.
Borman et al., "5-HT2B receptors play a key role in mediating the excitatory effects of 5-HT in human colon in vitro," *Br. J. Pharmacol.* (2002) vol. 135, No. 5, pp. 1144-1151.
Brann, M. R. "Identification of ligands by selective amplification of cells transfected with receptors and marker enzymes," *Chemical Abstracts* (1998) 128: 111548.
Choi et al., "5HT2B receptor-mediated serotonin morphogenic functions in mouse cranial neural crest and myocardiac cells," *Development* (1997) vol. 124, pp. 1745-1755.
Cirrito et al., "Serotonin signaling is associated with lower amyloid-β levels and plaques in transgenic mice and humans," *PNAS* (2011) vol. 108, No. 36, pp. 14968-14973.
Clinical Pharmacology and Biology Review(s), Application Number: 207318Orig1s000, Center for Drug Evaluation and Research, Submission Date Sep. 1, 2015 [available online Jun. 3, 2016]. Retrieved from the Internet: https://www.accessdata.fda.gov/drugsatfda_docs/nda/2016/207318Orig1s000ClinPharmR.pdf (88 pages).
Cummings et al., "Pimavanserin for patients with Parkinson's disease psychosis: a randomised, placebo-controlled phase 3 trial," *Lancet* (2014) vol. 383, pp. 533-540.
Database CA [online] Chemical Abstracts Service, Columbus, Ohio, US; 2016, Wang et al., "Intermediate ofpimavanserin and its analog, preparation method thereof and preparation method ofpimavanserin and its analog," XP002761533, retrieved from STN Database accession No. 2016:451070 (reference date: Mar. 23, 2016).
Database CA [online] Chemical Abstracts Service, Columbus, Ohio, US; 2016, Zheng, Xuchun et al: "A process for preparing pimavanserin tartrate," XP002761538, retrieved from STN Database accession No. 2016:1261850 (reference date: Aug. 3, 2016).
DeClerck, et al., "Increase in slow-wave sleep in humans with the serotonin-S2 antagonist ritanserin," *Current Therapeutic Research* (1987) 41(4):427-432.
Delecluse, et al., "A case of tardive tremor successfully treated with clozapine," *Movement Disorders* (1998) 13(5):846-847.
Dunn, et al., "Analgetic and antiinflammatory 7-aroylbenzofuran-5-ylacetic acids and 7-aroylbenzothiophene-5-ylacetic acids," *J. Med. Chem.* (1986) 29:2326-2329.
Durif, et al., "Low-dose clozapine improves dyskinesias in Parkinson's disease," *Neurology* (1997) 48:658-662.
Edited Transcript, "ACAD—ACADIA Pharmaceuticals Inc to discuss the FDA approval of Nuplazid," Thomson Reuters, May 2, 2016 (19 pages).
Eichelbaum, et al., "Influence of pharmacogenetics on drug disposition and response," *Clinical and Experimental Pharmacology and Physiology* (1996) 23:983-985.
Everett, et al., "L-Dopa: Effect on concentrations of dopamine, norepinephrine, and serotonin in brains of mice," *Science* (1970) 168:849-850.
Factor, et al. "Clozapine for the treatment of drug-induced psychosis in Parkinson's disease: Results of the 12 week open label extension in the PSYCLOPS trial," *Movement Disorders* (2001) 16(1):135-139.
Factor, et al., "Clozapine prevents recurrence of psychosis in Parkinson's disease," *Movement Disorders* (1992) 7(2):125-131.
Fitzgerald et al., "Possible Role of Vavular Serotonin 5-HT2B Receptors in the Cardiopathy Associated with Fenfluramine," *Molecular Pharmacol.* (1999) vol. 57, pp. 75-81.
Friedman et al., "A Multi-Center, Placebo-Controlled, Double-Blind Trial to Examine the Safety and Efficacy of Pimavanserin in the Treatment of Psychosis in Parkinson's Disease," *Neurology* (2010) vol. 74, No. 9, Suppl. 2, pp. A299.
Friedman, et al., "Atypical antipsychotics in the treatment of drug-induced psychosis in Parkinson's disease," *Movement Disorders* (2000) 15(2):201-211.
Friedman, et al., "Low-dose clozapine for the treatment of drug-induced psychosis in Parkinson's disease," *N. Engl. J. Med.* (1999) 340(10):757-763.
Friedman, J. H. "Clozapine treatment of psychosis in patients with tardive dystonia: Report of three cases," *Movement Disorders* (1994) 9(3):321-324.

(56) References Cited

OTHER PUBLICATIONS

Gillman, P. K. "Monoamine oxidase inhibitors, opioid analgesics and serotonin toxicity," *British Journal of Anaesthesia* (2005) 95(4):434-441.

Goldman et al., "Genetic counseling and testing for Alzheimer disease: Joint practice guidelines of the American College of Medical Genetics and the National Society of Genetic Counselors," *Genetics in Medicine* (2011) vol. 13, No. 6, pp. 597-605.

Hatoum, H. T. et al., "The Use of the Occupational Disruptiveness Scale of the Neuropsychiatric Inventory-Nusing Home Version to Measure the Impact of Rivastigmine on the Disruptive Behavior of Nursing Home Residents with Alzheimer's Disease," *Journal of the American Medical Directors Association* (2005) vol. 6, No. 4, pp. 238-245.

Highlights of Prescribing Information Nuplazid™ (pimavanserin), Revised Apr. 2016. Retrieved from the Internet (URL): https://www.accessdata.fda.gov/drugsatfda_docs/label/2016/207318lbl.pdf (14 pages).

Highlights of Prescribing Information Nuplazid® (pimavanserin), Revised Jun. 2018. Retrieved from the Internet (URL): https://www.accessdata.fda.gov/drugsatfda_docs/label/2018/207318s005lbl.pdf (15 pages).

Highlights of Prescribing Information Nuplazid® (pimavanserin), Revised Mar. 2018. Retrieved from the Internet (URL): https://www.accessdata.fda.gov/drugsatfda_docs/label/2018/207318s002s004lbl.pdf (15 pages).

Idzikowski, et al. 1991. A dose response study examining the effects of ritanserin on human slow wave sleep. Br. J. Clin. Pharmac., 31:193-196.Idzikowski, et al., "A dose response study examining the effects of ritanserin on human slow wave sleep," *Br. J. Clin. Pharmac.* (1991) 31:193-196.

International Search Report and Written Opinion in corresponding PCT Application PCT/US2016/042933 dated Oct. 14, 2016 (13 pages).

International Search Report and Written Opinion in corresponding PCT Patent Application No. PCT/US08/057557 dated Oct. 24, 2008 (10 pages).

International Search Report and Written Opinion in corresponding PCT Patent Application No. PCT/US2017/024526 dated Jul. 5, 2017 (18 pages).

International Search Report and Written Opinion in corresponding PCT Patent Application No. PCT/US2017/023795 dated May 29, 2017 (11 pages).

International Search Report and Written Opinion in corresponding PCT Patent Application No. PCT/US2017/066340 dated Mar. 5, 2018 (13 pages).

International Search Report and Written Opinion in corresponding PCT Patent Application No. PCT/US2018/029831 dated Jul. 11, 2018 (10 pages).

International Search Report and Written Opinion in corresponding PCT Patent Application No. PCT/US2018/048096 dated Oct. 30, 2018 (12 pages).

International Search Report and Written Opinion for International Application No. PCT/US2013/071792, dated, Jan. 1, 2014 (9 pages).

Ito et al., "Prediction of Human Drug Clearance from in Vitro and Preclinical Data Using Physiologically Based and Emperical Approaches," Pharm. Res., (2005) vol. 22, No. 1, pp. 103-112.

Kalgutkar, et al., "Selective inhibitors of monoamine oxidase (MAO-A and MAO-B) as probes of its catalytic site and mechanism," *Medicinal Research Reviews* (1995) 15(4)325-388.

Labeling, Application No. 207318Orig1s000, Center for Drug Evaluation and Research, Revised Apr. 2016 [available online Jun. 3, 2016]. Retrieved from the Internet (URL): https://www.accessdata.fda.gov/drugsatfda_docs/nda/2016/207318Orig1s000Lbl.pdf (19 pages).

Leysen, et al. "Serotonergic component of neuroleptic receptors," *Nature* (1978) 272:168-171.

Liechti, et al., "Effects of MDMA (ecstasy) on prepulse inhibition and habituation of startle in humans after pretreatment with Citalopram, Haloperidol, or Ketanserin," *Neuropsychopharmacology* (2001) 24(3):240-252.

Linder, et al. "Pharmacogenetics: A laboratory tool for optimizing therapeutic efficiency," *Clinical Chemistry* (1997) 43(2):254-266.

Marek et al., "The Selective 5-HT2A receptor Antagonist MI00907 Enhances Antidepressant-Like Behavioral Effects of the SSRI Fluoxetine," *Neuropsychopharmacology* (2005) vol. 30, No. 12, pp. 2205-2215.

Marek, et al., "Synergistic action of 5-HT2A antagonists and selective serotonin reuptake inhibitors. in neuropsychiatric disorders," *Neuropsychopharmacology* (2003) 28:402-412.

Medical Review(s), Application No. 207318Orig1s000, Center for Drug Evaluation and Research, Submission Date Sep. 1, 2015 [available online Jun. 3, 2016]. Retrieved from the Internet (URL): <https://www.accessdata.fda.gov/drugsatfda_docs/nda/2016/207318Orig1s000MedR.pdf> (173 pages).

Meltzer et al., "Co-therapy with pimavanserin and risperidone 2 mg provides an improved clinical profile," *Schizophrenia Research* (2008) vol. 98, pp. 16.

Meltzer et al., "Pimavanserin, a Serotonin(2A) Receptor Inverse Agonist, for the Treatment of Parkinson's Disease Psychosis," *Neuropsychopharmacology* (2010) vol. 35, No. 4, pp. 881-892.

Meltzer et al., "Serotonin Receptors: Their Key Role in Drugs to Treat Schizophrenia," *Progress in Neuro-Pyschopharmacology & Biol. Psych.* (2003) vol. 27, pp. 1159-1172.

Meltzer, et al., "Plasma clozapine levels and the treatment of L-DOPA-induced psychosis in Parkinson's disease," *Neuropsychopharmacology* (1995) 12(1):39-45.

Meltzer, H. Y. "The role of serotonin in antipsychotic drug action," *Neuropsychopharmacology* (1999) 21(2S): 106S-115S.

Morley et al., "Antibody to Amyloid p Protein Alleviates Imparied Acquisition, Retention, and Memory Processing in SAMP8 Mice," *Neurobiology of Learning and Memory* (2002), 78(1):125-138.

Naritomi et al., "Prediction of human hepatic clearance from in vivo animal experiments and in vitro metabolic studies with liver microsomes from animals and humans," *Drug Metab. Dispos.* (2001) vol. 29, No. 10, pp. 1316-1324.

NDA Approval/Supplement Approval, NDA 210793 NDA 207318/S-003, Letter Signed Jun. 28, 2018. Retrieved from the Internet (URL): https://www.accessdata.fda.gov/drugsatfda_docs/appletter/2018/210793Orig1s000,207318Orig1s003ltr.pdf (5 pages).

Nebigil et al., "Serotonin is a novel survival factor of cardiomyocytes: mitochondria as a tarqet of 5-HT2B-receptor signaling," *FASEB J.* (2003) vol. 27, No. 10, pp. 1373-1375.

Ng, et al., "L-dopa-induced release of cerebral monoamines," *Science* (1970) 170:76-77.

Nordstrom, et al., "High 5-HT2 receptor occupancy in clozapine treated patients demonstrated by PET," *Psychopharmacology* (1993) 110:365-367.

Norton et al., "Caregivers of PDP patients have an increased risk of developing emotional and social distress that is decreased when PDP is treated with pimavanserin," (Meeting Abstract) *Journal of Parkinson's Disease* (Sep. 2016) vol. 6, No. 51, pp. 257, Abstract No. P42.11.

Norton et al., "Decreased burden among caregivers of patients with Parkinson's disease psychosis (PDP) treated with pimavanserin, a selective 5-HT2A inverse agonist," (Meeting Abstract) *Journal of Parkinson's Disease* (Sep. 2016) vol. 6, No. 51, p. 88, Abstract No. P12.08.

Obach et al., "The Prediction of Human Pharmacolinetic Parameters from Preclinical and In Vitro Metabolism Data," *J. Pharm. Exp. Therap.* (1997) vol. 283, No. 1, pp. 46-58.

Office Director Memo, Application Number: 207318Orig1s000, Center for Drug Evaluation and Research, Submission Date Sep. 1, 2015 [available online Jun. 3, 2016]. Retrieved from the Internet (URL): https://www.accessdata.fda.gov/drugsatfda_docs/nda/2016/207318Orig1s000ODMemo.pdf (14 pages).

Ogawa, et al., "Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis," *European Journal of Pharmacology* (2005) 521:156-163.

Other Review(s), Application No. 207318Orig1s000, Center for Drug Evaluation and Research, Updated Apr. 29, 2016 [available

(56) References Cited

OTHER PUBLICATIONS online Jun. 3, 2016]. Retrieved from the Internet (URL): https://www.accessdata.fda.gov/drugsatfda_docs/nda/2016/207318Orig1s000OtherR.pdf (119 pages).
Paiva, et al., "Effects of ritanserin on sleep disturbances of dysthymic patients," *Psychopharmacology* (1988) 96:395-399.
Patel, et al., "The highly selective 5-hydroxytryptamine (5-HT)2A receptor antagonist, EMO 281014, significantly increases swimming and decreases immobility in male congenital learned helpless rats in the forced swim test," *Synapse* (2004) 52:73-75.
"Nuplazid™ (pimavanserin) Sponsor Background Information for a Meeting of the Psychopharmacologic Drugs Advisory Committee on Mar. 29, 2016," Acadia Pharmaceuticals Inc., 2016. Retrieved from the Internet (URL): <https://www.fda.gov/downloads/advisorycommittees/committeesmeetingmaterials/drugs/psychopharmacologicdrucgsadvisorycommittee/ucm492453.pdf> (173 pages).
Pharmacology Review(s), Application No. 207318Orig1s000, Center for Drug Evaluation and Research, Submission Date Sep. 1, 2015 [available online Jun. 3, 2016]. Retrieved from the Internet (URL): https://www.accessdata.fda.gov/drugsatfda_docs/nda/2016/207318Orig1s000PharmR.pdf (218 pages).
Pierce, et al., "5-hydroxytryptamine-induced synovial plasma extravasation is mediated via 5-hydroxytryptamine2A receptors on sympathetic efferent terminals," *The Journal of Pharmacology and Experimental Therapeutics* (1995) 275(1):502-508.
Poewe, W. "Psychosis in Parkinson's disease," *Movement Disorders* (2006) vol. 18, Suppl. 6, pp. S80-S87.
Pollak, et al., "Clozapine in drug-induced psychosis in Parkinson's disease," *Lancet* (1999) 353:2041-2042.
Price et al., "Pimavanserin, a 5-HT2A receptor inverse agonist, reverses psychosis-like behaviors in a rodent model of Alzheimer's disease," *Behavioural Pharmacology* (2002), 23:426-433.
R&D Focus Drug News (Jan. 24, 2000). Pimvaserin ACADIA lead compounds identified.
R&D Focus Drug News (Nov. 12, 2001). Pimvaserin ACADIA preclinical data.
Sadzot, et al., "Hallucinogenic drug interactions at human brain 5-HT2 receptors: Implications for treating LSD-induced hallucinogenesis," *Psychopharmacology* (1989) 98:495-499.
Saltzman, et al., "Cloning of the human serotonin 5-HT2 and 5-HT1C receptor subtypes," *Biochemical and Biophysical Research Communications* (1991) 181(3):1469-1478.
Saxena, et al., "Cardiovascular effects of serotonin agonists and antagonists," *Journal of Cardiovascular Pharmacology* (1990) 15(Supp. 7):S17-S34.
Shanmugam, S. "Granulation Techniques and Technologies: Recent Progresses," *BioImpacts* (2015) vol. 5, No. 1, pp. 55-63.
Stoner et al., "Integrated oral bioavailability projection using in vitro screening data as a selection tool in drug discovery," *Int. J. Pharm.* (2004) vol. 269, No. 1, pp. 241-249.
Summary Review, Application No. 207318Orig1s000, Center for Drug Evaluation and Research, Submission Date Sep. 1, 2015 [available online Jun. 3, 2016]. Retrieved from the Internet (URL): https://www.accessdata.fda.gov/drugsatfda_docs/nda/2016/207318Orig1s000SumR.pdf (20 pages).
Vanover et al., "Pharmacological Characterization of AC-90179 [2-(4-Methoxy-phenyl)-N-(4-methyl-benzyl)-N-(1-methyl-piperidiny-4-yl)-acetamide Hydrochloride]: A Selective Serotonin 2A Receptor Inverse Agonist," *J. Pharmacology & Experimental Therapeutics* (2004) vol. 310, No. 3, pp. 943-951.
Vanover, Kimberly E. et al., "Pharmacokinetics, tolerability, and safety of ACP-103 following single or multiple oral dose administration in healthy volunteers," *Journal of Clinical Phamacol.* (2007) vol. 47, No. 6, pp. 704-714.
Volk et al., "Synthesis of methyl ethyl and phenyl 4 2 methylpropoxy benzyl carbamates," The IP.com Prior Art Database, Disclosure No. IPCOM000244271D, (Nov. 27, 2015).

\* cited by examiner

COMBINATION OF PIMAVANSERIN AND CYTOCHROME P450 MODULATORS

CROSS REFERENCE TO RELATED APPLICATIONS

This application is a continuation of U.S. patent application Ser. No. 16/087,604 filed Sep. 21, 2018, which is a U.S. National Stage Application filed under 35 U.S.C. § 371 of International Patent Application No. PCT/US2017/023795, filed Mar. 23, 2017, which claims the benefit of and priority to U.S. Provisional Patent Application Nos. 62/313,674, filed Mar. 25, 2016, and 62/367,565, filed Jul. 27, 2016, and Swedish Patent Application No. 1630068-3, filed Apr. 4, 2016.

FIELD

The present disclosure relates generally to therapeutic use of pimavanserin or a pharmaceutical acceptable salt thereof. More specifically, the present disclosure provides methods for treating a disease or disorder by administering pimavanserin or a pharmaceutical acceptable salt thereof in a patient who is treated concurrently with a cytochrome P450 modulator.

BACKGROUND

New and effective pharmacological treatments for neuropsychiatric disorders continue to be an area of intense research.

Pimavanserin (formerly ACP-103) is a potent and selective 5-hydroxytryptamine (5-HT)$_{2A}$ receptor inverse agonist of interest as therapeutic for neuropsychiatric diseases and disorders, such as, for example, Parkinson's disease psychosis, sleep disorders, and schizophrenia. See, e.g., U.S. Pat. No. 7,601,740 B2; Vanover et al., *The Journal of Pharmacology and Experimental Therapeutics*, 2006, vol. 317, no. 2, pages 910-918. Preparations of pimavanserin and pimavanserin in salt and crystalline forms have been described in, for instance, U.S. Pat. No. 7,601,740 B2, WO 2006/037043 A1 and WO 2006/036874 A1. Tolerability and safety of pimavanserin has been studied in healthy volunteers, see, e.g., Vanover et al., *The Journal of Clinical Pharmacology*, 2007, vol. 47, no. 6, pages 704-714, and clinical studies with pimavanserin have been undertaken.

A demand exists for new doses and methods of administration of pimavanserin, for instance, to afford the improved therapeutic effect in a given patient population.

SUMMARY

Provided herein are methods for therapeutic use of pimavanserin or a pharmaceutically acceptable salt thereof. More specifically, the present disclosure provides methods for treating a disease or disorder by administering pimavanserin or a pharmaceutical acceptable salt thereof to a patient who has the disease or disorder and is being treated concurrently with a cytochrome P450 modulator, e.g., an inducer or an inhibitor.

In one aspect, provided herein is a method for treating a disease or disorder in a patient who is currently taking a cytochrome P450 inhibitor. In some embodiments, provided herein is a method for treating a disease or disorder in a patient who is currently taking a cytochrome P450 inhibitor comprising administering to the patient a dose of a compound of Formula (I) or a pharmaceutical acceptable salt thereof:

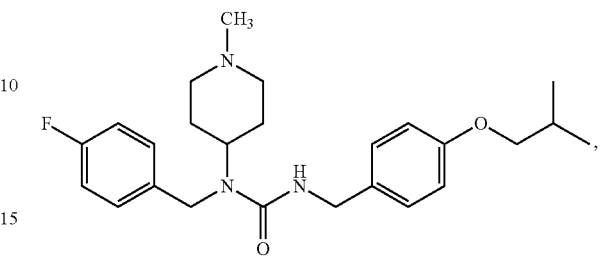

(I)

wherein the dose is at least 20% lower than a dose of the compound of Formula (I) or a pharmaceutical acceptable salt thereof that would otherwise have been recommended to the patient if the patient were not currently taking the cytochrome P450 inhibitor.

In some specific embodiments, the disease or disorder is Parkinson's disease psychosis or associated symptoms such as hallucinations or delusions. In other specific embodiments, the disease or disorder is Alzheimer's disease psychosis or associated symptoms, for example hallucinations or delusions. In yet other specific embodiments, the disease or disorder is schizophrenia or associated symptoms.

In some embodiments, the cytochrome P450 inhibitor is a cytochrome P450 3A (CYP3A) inhibitor. In some more specific embodiments, the cytochrome P450 inhibitor is a cytochrome P450 3A4 (CYP3A4) inhibitor and/or a cytochrome P450 3A5 (CYP3A5) inhibitor. In some more specific embodiments, wherein the cytochrome P450 inhibitor is a cytochrome P450 3A4 (CYP3A4) inhibitor. In other more specific embodiments, the cytochrome P450 inhibitor is a cytochrome P450 3A5 (CYP3A5) inhibitor.

In some embodiments, the cytochrome P450 inhibitor inhibits more than one CYP3A enzymes (non-specific or pan-specific inhibitors). For example, the cytochrome P450 inhibitor can be a non-specific inhibitor or a pan-specific inhibitor. In other embodiments, the cytochrome P450 inhibitor inhibits only one CYP3A enzyme. For example, the cytochrome P450 inhibitor can be a selective inhibitor, e.g., of CYP3A4.

In some embodiments, the cytochrome P450 inhibitor is a reversible inhibitor, e.g., ketoconazole. In other embodiments, the cytochrome P450 inhibitor is an irreversible inhibitor, e.g., clarithromycin.

In some embodiments, the cytochrome P450 inhibitor modulates only intestinal CYP3A, e.g., grapefruit juice. In other embodiments, the cytochrome P450 inhibitor modulates CYP3A in all tissues, e.g., ketoconazole.

In some embodiments, the cytochrome P450 inhibitor is a moderate inhibitor of the cytochrome P450, e.g., a CYP3A4 or CYP3A5 inhibitor. Exemplary moderate inhibitors provided herein include, but are not limited, to Aprepitant, Atazanavir/Ritonavir, Ciprofloxacin, Darunavir/Ritonavir, Diltiazem, Dronedarone, Erythromycin, Fluconazole, Grapefruit Juice, Imatinib, and Verapamil.

In other embodiments, the cytochrome P450 inhibitor is a strong inhibitor of the cytochrome P450. Exemplary strong inhibitors provided herein include, but are not limited to, Boceprevir, Clarithromycin, Cobicistat, Conivaptan, Indinavir, Itraconazole, Ketoconazole, Lopinavir/Ritonavir, Mibefradil, Nefazodone, Nelfinavir, Posaconazole, Ritonavir, Saquinavir, Telaprevir, Telithromycin, Troleandomycine and Voriconazole.

In other embodiments, the cytochrome P450 inhibitor is selected from the group consisting of Atazanavir, Darunavir, Fosamprenavir, Fluvoxamine, Lopinavir, and Quinupristin.

In some embodiments, the dose of the compound of Formula (I) or a pharmaceutical acceptable salt thereof is about 20% to 80% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 30% to 70% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 40% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 50% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 60% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor.

In other embodiments, the dose of the compound of Formula (I) or a pharmaceutical acceptable salt thereof is about 33% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In yet other embodiments, the dose of the compound of Formula (I) or a pharmaceutical acceptable salt thereof is about 66% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor.

In some embodiments, the compound of Formula (I) in a dose of less than 27 mg is administered to the patient. In other embodiments, the compound of Formula (I) in a dose of less than 23 mg is administered to the patient. In yet other embodiments, the compound of Formula (I) in a dose of less than 12 mg is administered to the patient. In yet other embodiments, the compound of Formula (I) in a dose of about 8.5-20 mg is administered to the patient. In yet other embodiments, the compound of Formula (I) in a dose of about 12-19 mg is administered to the patient. In yet other embodiments, the compound of Formula (I) in a dose of about 15-19 mg is administered to the patient. In a specific embodiment, the compound of Formula (I) in a dose of about 17 mg is administered to the patient.

In some embodiments, a pharmaceutical salt of the compound of Formula (I) is administered to the patient. In some specific embodiments, a tartrate salt of the compound of Formula (I) is administered to the patient.

In some embodiments, the tartrate salt of the compound of Formula (I) in a dose of less than 32 mg is administered to the patient. In other embodiments, the tartrate salt of the compound of Formula (I) in a dose of less than 27 mg is administered to the patient. In yet other embodiments, the tartrate salt of the compound of Formula (I) in a dose of less than 14 mg is administered to the patient. In yet other embodiments, the tartrate salt of the compound of Formula (I) in a dose of about 10-24 mg is administered to the patient. In a specific embodiment, the tartrate salt of the compound of Formula (I) in a dose of about 20 mg is administered to the patient.

In some embodiments, the tartrate salt of the compound of Formula (I) is administered daily. In some embodiments, the tartrate salt of compound of Formula (I) is administered once daily. In some embodiments, the tartrate salt of compound of Formula (I) is formulated for oral administration as a unit dose. In a specific embodiment, the unit dose is a tablet.

In some embodiments, the tartrate salt of the compound of Formula (I) is in a crystalline form, wherein the crystalline form of the tartrate salt of the compound of Formula (I) exhibits a X-ray powder diffraction pattern comprising peaks having d-values in angstroms (Å) of about 10.7, about 4.84, about 4.57, and about 3.77.

In some embodiments, the dose of the compound of Formula (I) or a pharmaceutical acceptable salt thereof that would otherwise have been recommended to the patient if the patient were not currently taking the cytochrome P450 inhibitor is a manufacturer's recommended dose in the absence of concomitant administration of the cytochrome P450 inhibitor.

In another aspect, provided herein is a method for treating a disease or disorder in a patient who is currently taking pimavanserin or a pharmaceutical acceptable salt thereof. In some embodiments, provided herein is a method for treating a disease or disorder in a patient who is currently taking a first dose of a compound of Formula (I) or a pharmaceutical acceptable salt thereof:

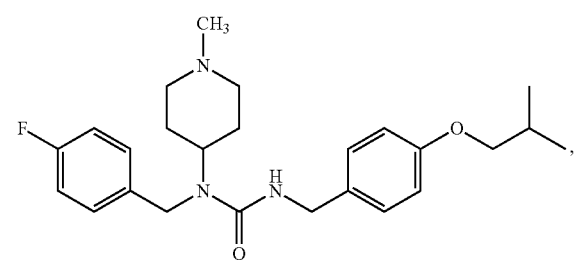

comprising:
administering to the patient a cytochrome P450 inhibitor, e.g., a CYP3A4 or CYP3A5 inhibitor; and
reducing the first dose to a second dose of the compound of Formula (I) or a pharmaceutical acceptable salt thereof, wherein the second dose is at least 20% lower than the first dose.

In some specific embodiments, the disease or disorder is Parkinson's disease psychosis or associated symptoms such as hallucinations or delusions. In other specific embodiments, the disease or disorder is Alzheimer's disease psychosis or associated symptoms. In yet other specific embodiments, the disease or disorder is schizophrenia or associated symptoms.

In some embodiments, the cytochrome P450 inhibitor is a cytochrome P450 3A (CYP3A) inhibitor. In some more specific embodiments, the cytochrome P450 inhibitor is a cytochrome P450 3A4 (CYP3A4) inhibitor and/or cytochrome P450 3A5 (CYP3A5) inhibitor. In some more specific embodiments, wherein the cytochrome P450 inhibitor is a cytochrome P450 3A4 (CYP3A4) inhibitor. In other more specific embodiments, the cytochrome P450 inhibitor is a cytochrome P450 3A5 (CYP3A5) inhibitor.

In some embodiments, the cytochrome P450 inhibitor is a moderate inhibitor of the cytochrome P450, e.g., a CYP3A4 or CYP3A5 inhibitor. Exemplary moderate inhibitors provided herein include, but are not limited, to Aprepitant, Atazanavir/Ritonavir, Ciprofloxacin, Darunavir/Ritonavir, Diltiazem, Dronedarone, Erythromycin, Fluconazole, Grapefruit Juice, Imatinib, and Verapamil.

In other embodiments, the cytochrome P450 inhibitor is a strong inhibitor of the cytochrome P450. Exemplary strong inhibitors provided herein include, but are not limited to, Boceprevir, Clarithromycin, Cobicistat, Conivaptan, Indinavir, Itraconazole, Ketoconazole, Lopinavir/Ritonavir, Mibefradil, Nefazodone, Nelfinavir, Posaconazole, Ritonavir, Saquinavir, Telaprevir, Telithromycin, Troleandomycine and Voriconazole.

In other embodiments, the cytochrome P450 inhibitor is selected from the group consisting of Atazanavir, Darunavir, Fosamprenavir, Fluvoxamine, Lopinavir, and Quinupristin.

In some embodiments, the second dose of the compound of Formula (I) or a pharmaceutical acceptable salt thereof is about 20% to 80% less than the first dose of the compound of Formula (I) or a pharmaceutical acceptable salt thereof. In some embodiments, the second dose of the compound of Formula (I) or a pharmaceutical acceptable salt thereof is about 30% to 70% less than the first dose of the compound of Formula (I) or a pharmaceutical acceptable salt thereof. In some embodiments, the second dose of the compound of Formula (I) or a pharmaceutical acceptable salt thereof is about 40% less than the first dose of the compound of Formula (I) or a pharmaceutical acceptable salt thereof. In other embodiments, the second dose of the compound of Formula (I) or a pharmaceutical acceptable salt thereof is about 50% less than the first dose of the compound of Formula (I) or a pharmaceutical acceptable salt thereof. In other embodiments, the second dose of the compound of Formula (I) or a pharmaceutical acceptable salt thereof is about 60% less than the first dose of the compound of Formula (I) or a pharmaceutical acceptable salt thereof.

In other embodiments, the second dose of the compound of Formula (I) or a pharmaceutical acceptable salt thereof is about 33% less than the first dose of the compound of Formula (I) or a pharmaceutical acceptable salt thereof. In yet other embodiments, the second dose of the compound of Formula (I) or a pharmaceutical acceptable salt thereof is about 66% less than the first dose of the compound of Formula (I) or a pharmaceutical acceptable salt thereof.

In some embodiments, the compound of Formula (I) in a dose of less than 27 mg is administered to the patient. In other embodiments, the compound of Formula (I) in a dose of less than 23 mg is administered to the patient. In yet other embodiments, the compound of Formula (I) in a dose of less than 12 mg is administered to the patient. In yet other embodiments, the compound of Formula (I) in a dose of about 8.5-20 mg is administered to the patient. In yet other embodiments, the compound of Formula (I) in a dose of about 12-19 mg is administered to the patient. In yet other embodiments, the compound of Formula (I) in a dose of about 15-19 mg is administered to the patient. In a specific embodiment, the compound of Formula (I) in a dose of about 17 mg is administered to the patient.

In some embodiments, a pharmaceutical salt of the compound of Formula (I) is administered to the patient. In some specific embodiments, a tartrate salt of the compound of Formula (I) is administered to the patient.

In some embodiments, the second dose of the tartrate salt of the compound of Formula (I) of less than 32 mg is administered to the patient. In other embodiments, the second dose of the tartrate salt of the compound of Formula (I) of less than 27 mg is administered to the patient. In yet other embodiments, the second dose of the tartrate salt of the compound of Formula (I) of less than 14 mg is administered to the patient. In yet other embodiments, the second dose of the tartrate salt of the compound of Formula (I) of about 10-24 mg is administered to the patient. In a specific embodiment, the second dose of the tartrate salt of the compound of Formula (I) of about 20 mg is administered to the patient.

In some embodiments, the tartrate salt of the compound of Formula (I) is administered daily. In some embodiments, the tartrate salt of compound of Formula (I) is administered once daily. In some embodiments, the tartrate salt of compound of Formula (I) is formulated for oral administration as a unit dose. In a specific embodiment, the unit dose is a tablet.

In some embodiments, the tartrate salt of the compound of Formula (I) is in a crystalline form, wherein the crystalline form of the tartrate salt of the compound of Formula (I) exhibits a X-ray powder diffraction pattern comprising peaks having d-values in angstroms (Å) of about 10.7, about 4.84, about 4.57, and about 3.77.

In some embodiments, the first dose of the compound of Formula (I) or a pharmaceutical acceptable salt is a manufacturer's recommended dose in the absence of concomitant administration of the cytochrome P450 inhibitor.

In yet another aspect, provided herein is a compound of Formula (I) or a pharmaceutical acceptable salt thereof:

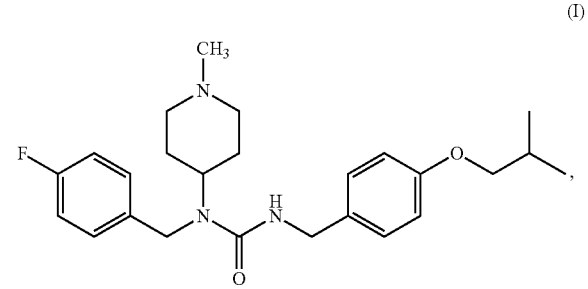 [SMILES: CC(C)COc1ccc(CNC(=O)N(Cc2ccc(F)cc2)C2CCN(C)CC2)cc1]

(I)

for treating a disease or disorder in a subject on a cytochrome P450 inhibitor, wherein the dose of the compound of Formula (I) or a pharmaceutical acceptable salt thereof is at least 20% lower than a dose of the compound of Formula (I) or a pharmaceutical acceptable salt thereof that would otherwise have been recommended to the patient if the patient were not on the cytochrome P450 inhibitor.

In some specific embodiments, the disease or disorder is Parkinson's disease psychosis or associated symptoms such as hallucinations or delusions. In other specific embodiments, the disease or disorder is Alzheimer's disease psychosis or associated symptoms, for example hallucinations or delusions. In yet other specific embodiments, the disease or disorder is schizophrenia or associated symptoms.

In some embodiments, the cytochrome P450 inhibitor is a cytochrome P450 3A (CYP3A) inhibitor. In some more specific embodiments, the cytochrome P450 inhibitor is a cytochrome P450 3A4 (CYP3A4) inhibitor and/or a cytochrome P450 3A5 (CYP3A5) inhibitor. In some more specific embodiments, wherein the cytochrome P450 inhibitor is a cytochrome P450 3A4 (CYP3A4) inhibitor. In other more specific embodiments, the cytochrome P450 inhibitor is a cytochrome P450 3A5 (CYP3A5) inhibitor.

In some embodiments, the cytochrome P450 inhibitor is a moderate inhibitor of the cytochrome P450, e.g., a CYP3A4 or CYP3A5 inhibitor. Exemplary moderate inhibitors provided herein include, but are not limited, to Aprepitant, Atazanavir/Ritonavir, Ciprofloxacin, Darunavir/Ritonavir, Diltiazem, Dronedarone, Erythromycin, Fluconazole, Grapefruit Juice, Imatinib, and Verapamil.

In other embodiments, the cytochrome P450 inhibitor is a strong inhibitor of the cytochrome P450. Exemplary strong inhibitors provided herein include, but are not limited to, Boceprevir, Clarithromycin, Cobicistat, Conivaptan, Indinavir, Itraconazole, Ketoconazole, Lopinavir/Ritonavir, Mibefradil, Nefazodone, Nelfinavir, Posaconazole, Ritonavir, Saquinavir, Telaprevir, Telithromycin, Troleandomycine and Voriconazole.

In other embodiments, the cytochrome P450 inhibitor is selected from the group consisting of Atazanavir, Darunavir, Fosamprenavir, Fluvoxamine, Lopinavir, and Quinupristin.

In some embodiments, the dose of the compound of Formula (I) or a pharmaceutical acceptable salt thereof is about 20% to 80% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 30% to 70% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 40% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 50% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 60% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor.

In other embodiments, the dose of the compound of Formula (I) or a pharmaceutical acceptable salt thereof is about 33% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In yet other embodiments, the dose of the compound of Formula (I) or a pharmaceutical acceptable salt thereof is about 66% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor.

In some embodiments, the compound of Formula (I) in a dose of less than 27 mg is administered to the patient. In other embodiments, the compound of Formula (I) in a dose of less than 23 mg is administered to the patient. In yet other embodiments, the compound of Formula (I) in a dose of less than 12 mg is administered to the patient. In yet other embodiments, the compound of Formula (I) in a dose of about 8.5-20 mg is administered to the patient. In yet other embodiments, the compound of Formula (I) in a dose of about 12-19 mg is administered to the patient. In yet other embodiments, the compound of Formula (I) in a dose of about 15-19 mg is administered to the patient. In a specific embodiment, the compound of Formula (I) in a dose of about 17 mg is administered to the patient.

In some embodiments, a pharmaceutical salt of the compound of Formula (I) is administered to the patient. In some specific embodiments, a tartrate salt of the compound of Formula (I) is administered to the patient.

In some embodiments, the tartrate salt of the compound of Formula (I) in a dose of less than 32 mg is administered to the patient. In other embodiments, the tartrate salt of the compound of Formula (I) in a dose of less than 27 mg is administered to the patient. In yet other embodiments, the tartrate salt of the compound of Formula (I) in a dose of less than 14 mg is administered to the patient. In yet other embodiments, the tartrate salt of the compound of Formula (I) in a dose of about 10-24 mg is administered to the patient. In a specific embodiment, the tartrate salt of the compound of Formula (I) in a dose of about 20 mg is administered to the patient.

In some embodiments, the tartrate salt of the compound of Formula (I) is administered daily. In some embodiments, the tartrate salt of compound of Formula (I) is administered once daily. In some embodiments, the tartrate salt of compound of Formula (I) is formulated for oral administration as a unit dose. In a specific embodiment, the unit dose is a tablet.

In some embodiments, the tartrate salt of the compound of Formula (I) is in a crystalline form, wherein the crystalline form of the tartrate salt of the compound of Formula (I) exhibits a X-ray powder diffraction pattern comprising peaks having d-values in angstroms (Å) of about 10.7, about 4.84, about 4.57, and about 3.77.

In some embodiments, the dose of the compound of Formula (I) or a pharmaceutical acceptable salt thereof that would otherwise have been recommended to the patient if the patient were not currently taking the cytochrome P450 inhibitor is a manufacturer's recommended dose in the absence of concomitant administration of the cytochrome P450 inhibitor.

In yet another aspect, provided herein is a use of a compound of Formula (I) or a pharmaceutical acceptable salt thereof:

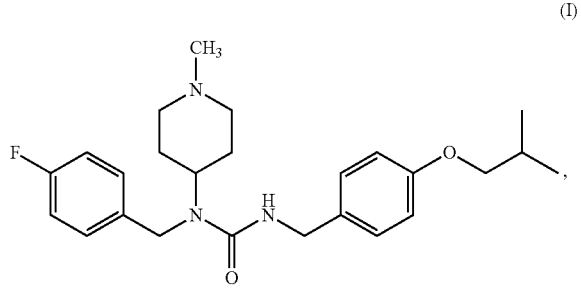 [SMILES: CC(C)COc1ccc(CNC(=O)N(Cc2ccc(F)cc2)C2CCN(C)CC2)cc1]

(I)

for the manufacture of a medicament for use in treating a disease or disorder in a subject on a cytochrome P450 inhibitor, wherein the dose of the compound of Formula (I) or a pharmaceutical acceptable salt thereof is at least 20% lower than a dose of the compound of Formula (I) or a pharmaceutical acceptable salt thereof that would otherwise have been recommended to the patient if the patient were not on the cytochrome P450 inhibitor.

In some specific embodiments, the disease or disorder is Parkinson's disease psychosis or associated symptoms such as hallucinations or delusions. In other specific embodiments, the disease or disorder is Alzheimer's disease psychosis or associated symptoms. In yet other specific embodiments, the disease or disorder is schizophrenia or associated symptoms.

In some embodiments, the cytochrome P450 inhibitor is a cytochrome P450 3A (CYP3A) inhibitor. In some more specific embodiments, the cytochrome P450 inhibitor is a cytochrome P450 3A4 (CYP3A4) inhibitor and/or a cytochrome P450 3A5 (CYP3A5) inhibitor. In some more specific embodiments, wherein the cytochrome P450 inhibitor is a cytochrome P450 3A4 (CYP3A4) inhibitor. In other more specific embodiments, the cytochrome P450 inhibitor is a cytochrome P450 3A5 (CYP3A5) inhibitor.

In some embodiments, the cytochrome P450 inhibitor is a moderate inhibitor of the cytochrome P450, e.g., a CYP3A4 or CYP3A5 inhibitor. Exemplary moderate inhibitors provided herein include, but are not limited to, Aprepitant, Atazanavir/Ritonavir, Ciprofloxacin, Darunavir/Ritonavir, Diltiazem, Dronedarone, Erythromycin, Fluconazole, Grapefruit Juice, Imatinib, and Verapamil.

In other embodiments, the cytochrome P450 inhibitor is a strong inhibitor of the cytochrome P450. Exemplary strong inhibitors provided herein include, but are not limited to, Boceprevir, Clarithromycin, Cobicistat, Conivaptan, Indinavir, Itraconazole, Ketoconazole, Lopinavir/Ritonavir, Mibefradil, Nefazodone, Nelfinavir, Posaconazole, Ritonavir, Saquinavir, Telaprevir, Telithromycin, Troleandomycine and Voriconazole.

In other embodiments, the cytochrome P450 inhibitor is selected from the group consisting of Atazanavir, Darunavir, Fosamprenavir, Fluvoxamine, Lopinavir, and Quinupristin.

In some embodiments, the dose of the compound of Formula (I) or a pharmaceutical acceptable salt thereof is about 20% to 80% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 30% to 70% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 40% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 50% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In some embodiments, the dose of the compound of Formula (I) or a pharmaceutical acceptable salt thereof is about 60% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor.

In other embodiments, the dose of the compound of Formula (I) or a pharmaceutical acceptable salt thereof is about 33% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor. In yet other embodiments, the dose of the compound of Formula (I) or a pharmaceutical acceptable salt thereof is about 66% less than the dose of the compound of Formula (I) or a pharmaceutical acceptable salt thereof that would otherwise have been recommended to the patient if the patient were not currently taking the cytochrome P450 inhibitor, e.g., a CYP3A4 or CYP3A5 inhibitor.

In some embodiments, the compound of Formula (I) in a dose of less than 27 mg is administered to the patient. In other embodiments, the compound of Formula (I) in a dose of less than 23 mg is administered to the patient. In yet other embodiments, the compound of Formula (I) in a dose of less than 12 mg is administered to the patient. In yet other embodiments, the compound of Formula (I) in a dose of about 8.5-20 mg is administered to the patient. In yet other embodiments, the compound of Formula (I) in a dose of about 12-19 mg is administered to the patient. In yet other embodiments, the compound of Formula (I) in a dose of about 15-19 mg is administered to the patient. In a specific embodiment, the compound of Formula (I) in a dose of about 17 mg is administered to the patient.

In some embodiments, a pharmaceutical salt of the compound of Formula (I) is administered to the patient. In some specific embodiments, a tartrate salt of the compound of Formula (I) is administered to the patient.

In some embodiments, the tartrate salt of the compound of Formula (I) in a dose of less than 32 mg is administered to the patient. In other embodiments, the tartrate salt of the compound of Formula (I) in a dose of less than 27 mg is administered to the patient. In yet other embodiments, the tartrate salt of the compound of Formula (I) in a dose of less than 14 mg is administered to the patient. In yet other embodiments, the tartrate salt of the compound of Formula (I) in a dose of about 10-24 mg is administered to the patient. In a specific embodiment, the tartrate salt of the compound of Formula (I) in a dose of about 20 mg is administered to the patient.

In some embodiments, the tartrate salt of the compound of Formula (I) is administered daily. In some embodiments, the tartrate salt of compound of Formula (I) is administered once daily. In some embodiments, the tartrate salt of compound of Formula (I) is formulated for oral administration as a unit dose. In a specific embodiment, the unit dose is a tablet.

In some embodiments, the tartrate salt of the compound of Formula (I) is in a crystalline form, wherein the crystalline form of the tartrate salt of the compound of Formula (I) exhibits a X-ray powder diffraction pattern comprising peaks having d-values in angstroms (Å) of about 10.7, about 4.84, about 4.57, and about 3.77.

In some embodiments, the dose of the compound of Formula (I) or a pharmaceutical acceptable salt thereof that would otherwise have been recommended to the patient if the patient were not currently taking the cytochrome P450 inhibitor is a manufacturer's recommended dose in the absence of concomitant administration of the cytochrome P450 inhibitor.

DETAILED DESCRIPTION

The present disclosure provides methods for treating a disease or disorder (such as neurodegenerative disease or neuropsychiatric diseases) by administering pimavanserin or a pharmaceutical acceptable salt thereof to a patient who has the disease or disorder and is being treated concurrently with a cytochrome P450 (CYP) modulator, e.g., an inducer or an inhibitor.

Results provided herein support that co-administration of a CYP modulator results in changed pimavanserin exposure as compared with that for administration of pimavanserin alone. For example, as shown in the Example below, ketoconazole co-administration resulted in higher pimavanserin exposure compared with that for administration of pimavanserin alone.

Provided herein is a method for treating a disease or disorder in a patient who is concurrently taking a CYP modulator, e.g., a CYP3A4 and/or CYP3A5 inhibitor, comprising administering to the patient a dose of pimavanserin or a pharmaceutical acceptable salt thereof, wherein the dose is different from a dose of pimavanserin or a pharmaceutical acceptable salt thereof that would otherwise have been recommended to the patient if the patient were not concurrently taking the CYP modulator.

In some embodiments, the cytochrome P450 (CYP) modulator is an inducer, an inhibitor, or a suppressor.

In some embodiments, provided herein is a method for modifying the dose of pimavanserin given to a patient in need thereof, wherein the dose is (1) increased if the patient is also taking a CYP inducer, and (2) reduced if the patient is also taking a CYP inhibitor or suppressor.

In one aspect, the co-administered CYP modulator is an inducer of a CYP. In some embodiments, provided herein is a method for treating a disease or disorder in patient who is concurrently taking a CYP inducer comprising administering to the patient a dose of pimavanserin or a pharmaceutical acceptable salt thereof, wherein the dose is different from a dose of pimavanserin or a pharmaceutical acceptable salt thereof that would otherwise have been recommended to the patient if the patient were not concurrently taking the CYP inducer. In some embodiments, the dose is higher than a dose of pimavanserin or a pharmaceutical acceptable salt thereof that would otherwise have been recommended to the patient if the patient were not concurrently taking the CYP inducer.

In another aspect, the co-administered CYP modulator is an inhibitor of a CYP. In some embodiments, provided herein is a method for treating a disease or disorder in patient who is concurrently taking a CYP inhibitor comprising administering to the patient a dose of pimavanserin or a pharmaceutical acceptable salt thereof, wherein the dose is different from a dose of pimavanserin or a pharmaceutical acceptable salt thereof that would otherwise have been recommended to the patient if the patient were not concurrently taking the CYP inhibitor. In some embodiments, the dose is lower than a dose of pimavanserin or a pharmaceutical acceptable salt thereof that would otherwise have been recommended to the patient if the patient were not concurrently taking the CYP inhibitor.

In another aspect, the co-administered CYP modulator is a suppressor of a CYP. In some embodiments, provided herein is a method for treating a disease or disorder in patient who is concurrently taking a CYP suppressor comprising administering to the patient a dose of pimavanserin or a pharmaceutical acceptable salt thereof, wherein the dose is different from a dose of pimavanserin or a pharmaceutical acceptable salt thereof that would otherwise have been recommended to the patient if the patient were not concurrently taking the CYP suppressor. In some embodiments, the dose is lower than a dose of pimavanserin or a pharmaceutical acceptable salt thereof that would otherwise have been recommended to the patient if the patient were not concurrently taking the CYP suppressor. In some embodiments, the CYP suppressor provided herein decreases CYP activity by lowering the level of that CYP enzyme. For example, suppressors of CYP3A can be various biologics such as antibodies, cytokines and other therapeutic proteins, and include, but are not limited to, basiliximab, muromonab-CD3, tocilizumab, IL-1, IL-2, IL-6, and IL-10.

In some embodiments, the patient has been taking a CYP modulator before pimavanserin or a pharmaceutical acceptable salt thereof is administered to the patient. Thus, in some specific embodiments, provided herein is a method for treating a disease or disorder in a patient who is currently taking a CYP inhibitor comprising administering to the patient a dose of pimavanserin or a pharmaceutical acceptable salt thereof, wherein the dose is lower than a dose of pimavanserin or a pharmaceutical acceptable salt thereof that would otherwise have been recommended to the patient if the patient were not currently taking the CYP inhibitor. In some embodiments, the dose of pimavanserin or a pharmaceutical acceptable salt thereof that would otherwise have been recommended to the patient if the patient were not currently taking the CYP inhibitor is a manufacturer's recommended dose in the absence of concomitant administration of the CYP inhibitor.

In other embodiments, the patient has been taking pimavanserin or a pharmaceutical acceptable salt thereof before a CYP modulator is administered to the patient. Thus, in some embodiments, provided herein is a method for treating a disease or disorder in a patient who is currently taking a first dose of pimavanserin or a pharmaceutical acceptable salt thereof comprising: administering to the patient a CYP inhibitor; and reducing the first dose to a second dose of pimavanserin or a pharmaceutical acceptable salt thereof. In some embodiments, the first dose of pimavanserin or a pharmaceutical acceptable salt thereof is a manufacturer's recommended dose in the absence of concomitant administration of the CYP inhibitor.

As used in the present disclosure, the term "first dose" and the term "second dose" are used in reference to each other. For instance, a "first dose" means a dose used before a "second dose." A "first dose" may, or may not be the first dose in a drug dosage treatment regimen.

It will be understood that, in certain embodiments of the methods provided herein to treat a disease or disorder in a patient, the patient to be administered with pimavanserin, or a pharmaceutically acceptable salt thereof, is on a CYP modulator therapy to treat a disease, disorder or condition that is different from the disease or disorder to be treated by administration of pimavanserin, or pharmaceutically acceptable salt thereof.

In some embodiments, a patient on a CYP modulator therapy to treat a disease or disorder is administered with pimavanserin or a pharmaceutically acceptable salt thereof, to treat the same disease or disorder.

In certain embodiments of the methods provided herein, no dose adjustment for the CYP modulator, e.g., CYP inhibitor or CYP inducer, is made when pimavanersin is co-administered to the patient.

Pimavanserin is N-(1-methylpiperidin-4-yl)-N-(4-fluorophenylmethyl)-N'-(4-(2-methylpropyloxy)phenylmethyl) carbamide, and has the structure of Formula (I):

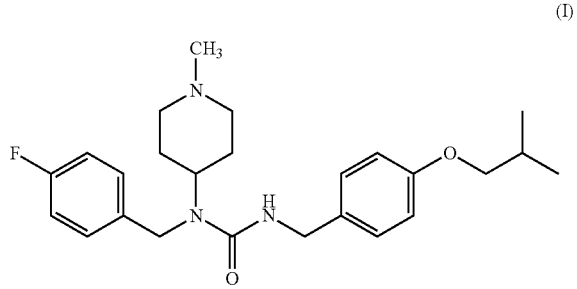 [SMILES: CC(C)COc1ccc(CNC(=O)N(Cc2ccc(F)cc2)C2CCN(C)CC2)cc1]

(I)

Pimavanserin may be synthesized by methods described in U.S. Pat. No. 7,601,740 (see columns 22-26), which is incorporated herein by reference in its entirety. In a specific embodiment, pimavanserin is prepared as shown in Scheme I below, or by modification of these methods. Ways of modifying the methodology include, among others, modification in temperature, solvent, reagents, etc., as will be known to those skilled in the art.

Pimavanserin can be present in a number of salts and crystalline forms which are included in the present disclosure.

Exemplary salts include the tartrate, hemi-tartrate, citrate, fumarate, maleate, malate, phosphate, succinate, sulphate, and edisylate (ethanedisulfonate) salts. Pimavanserin salts including the aforementioned ions, among others, are described in U.S. Pat. No. 7,868,176, which is incorporated herein by reference in its entirety.

The term "pharmaceutically acceptable salt" refers to a salt of a compound that does not cause significant irritation to an organism to which it is administered and does not abrogate the biological activity and/or properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid.

Scheme I: Synthesis of Pimavanserin

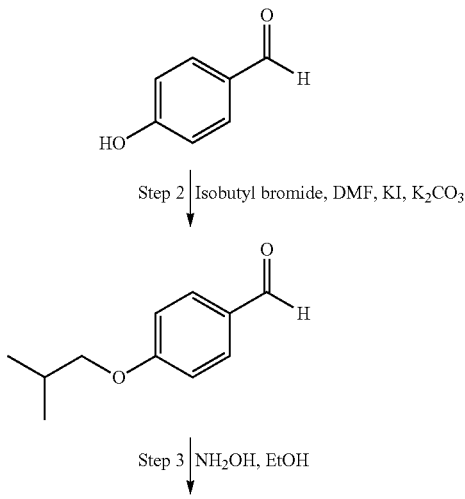

-continued
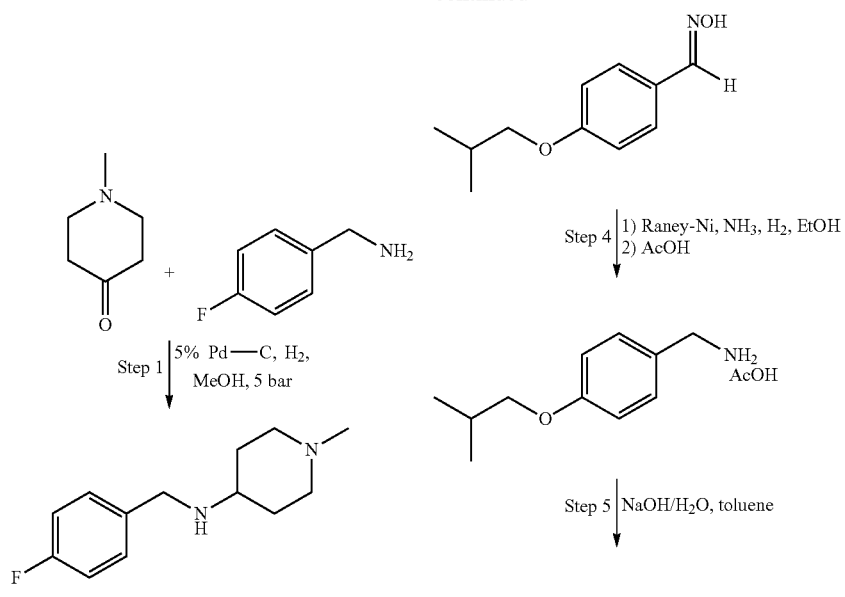
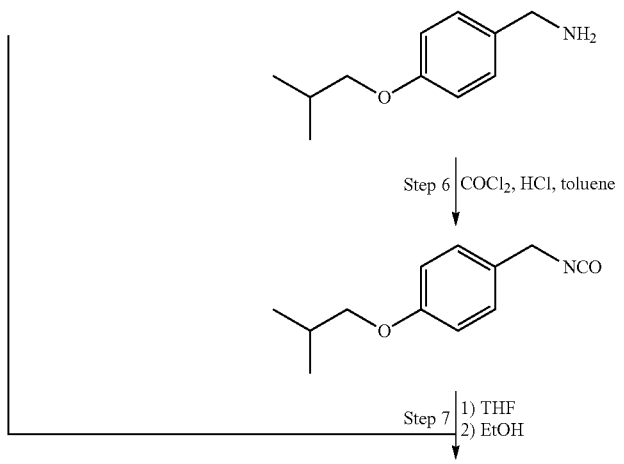
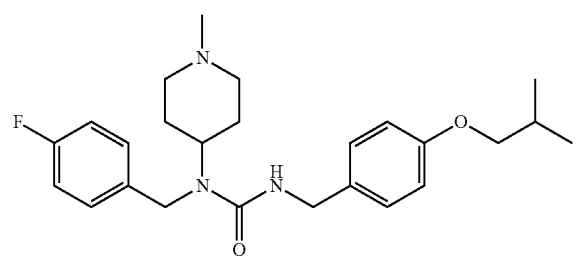

In certain embodiments, the pharmaceutically acceptable salt of pimavanserin is a tartrate salt of pimavanserin. In some embodiments, the pimavanserin tartrate salt can, for example, be urea, N-[(4-fluorophenyl)methyl]-N-(1-methyl-4-piperidinyl)-N'-[[4-(2-methylpropoxy)phenyl]methyl]-, (2R,3R)-2,3-dihydroxybutanedioate (2:1), which has the following chemical structure:

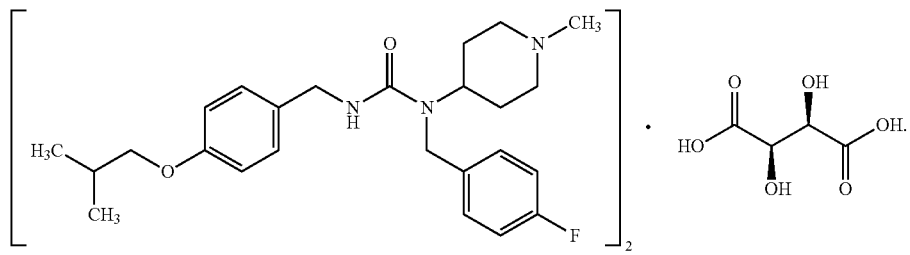

Several crystalline forms of the tartrate salt are referred to as crystalline Form A, Form B, Form C, Form D, Form E and Form F, and are described in U.S. Pat. No. 7,732,615, which is incorporated herein by reference in its entirety. In one embodiment, the crystalline form of the tartrate salt of pimavanserin is Form C, which exhibits an X-ray powder diffraction pattern comprising peaks having d-values in angstroms (Å) of about 10.7, about 4.84, about 4.57, and about 3.77. Specifically the X-ray powder diffraction pattern of Form C exhibits the following characteristic peaks expressed in d-values (Å): 12.0 (w), 10.7 (vs), 7.4 (vw), 6.9 (vw), 6.6 (vw), 6.2 (w), 5.86 (m), 5.53 (w), 5.28 (m), 5.16 (m), 4.84 (vs), 4.70 (m), 4.57 (s), 4.38 (m), 4.09 (w), 3.94 (w), 3.77 (s), 3.71 (m), 3.49 (w), 3.46 (w), 3.25 (w), 3.08 (w), and 2.93 (w). In various embodiments, Form C is present in a solid form of pimavanserin in amounts of at least about 50%, 70%, 80%, 90%, 95%, or 98%, with the remainder being other crystalline forms (including hydrates and solvates) and/or amorphous forms.

Pimavanserin (including, for example, the tartrate salt) may be formulated into tablets, such as is described in more detail in U.S. Pat. No. 7,790,899, and U.S. Patent Publication No. 2007-0264330, filed May 15, 2007, each entitled "PHARMACEUTICAL FORMULATIONS OF PIMAVANSERIN," which are incorporated herein by reference in their entireties.

The present disclosure provides methods for administering pimavanserin or a pharmaceutically acceptable salt thereof concurrently with administration of an inhibitor of cytochrome P450 (CYP). CYP represents a superfamily of heme-containing enzymes responsible for the biotransformation (metabolism) of many endogenous compounds (endobiotics) and foreign compounds (xenobiotics) including numerous drugs. In mammals, CYP enzymes are largely located in the smooth endoplasmic reticulum (microsomes) and mitochondria of a wide range of organs and tissues. The CYP enzymes involved in drug metabolism are located in the liver and numerous extrahepatic tissues including the gastrointestinal tract, kidney, lung, skin and many others.

The CYP modulators provided herein include modulators of a CYP selected from the CYP families of CYP1, CYP2, CYP3, CYP4, CYP5, CYP7, CYP8, CYP11, CYP17, CYP19, CYP20, CYP21, CYP24, CYP26, CYP27, CYP39, CYP46, CYP51.

In some embodiments, the CYP modulator provided herein is modulator of a CYP selected from the group consisting of CYP1A1, CYP1A2, CYP1B1, CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1, CYP3A4, CYP3A5, CYP3A7, CYP3A43, CYP4A11, CYP4A22, CYP4B1, CYP4F2, CYP4F3, CYP4F8, CYP4F11, CYP4F12, CYP4F22, CYP4V2, CYP4X1, CYP4Z1, CYP5A1, CYP7A1, CYP7B1, CYP8A1, CYP8B1, CYP11A1, CYP11B1, CYP11B2, CYP17A1, CYP19A1, CYP20A1, CYP21A2, CYP24A1, CYP26A1, CYP26B1, CYP26C1, CYP27A1, CYP27B1, CYP27C1, CYP39A1, CYP46A1, and CYP51A1.

In some more specific embodiments, the CYP modulator provided herein is a CYP3 modulator. Members of the CYP3A subfamily are expressed at relatively high levels in the liver, gastrointestinal tract and respiratory tract of humans and other vertebrates, where they biotransform (metabolize) a wide variety of chemically diverse compounds including endobiotics (such as steroids) and xenobiotics (such as drugs). The catalytic activities of CYP3A enzymes are diverse, including, but not limited to, hydroxylation, epoxidation, oxygenation, dehydrogenation, dealkylation (and other types of bond cleavage) and rearrangement reactions, all of which are subject to inhibition.

In some embodiments, the CYP3 modulator is a CYP3A inducer. In some embodiments, the CYP3A inducer is selected from the group consisting of rifampicin (rifampin), rifabutin, glucocorticoids (such as dexamethasone), carbamazepine, phenobarbital, phenytoin, St. John's wort, artemisinin, and nevirapine.

In other embodiments, the CYP3 modulator is a CYP3A inhibitor. In a specific embodiment, the CYP3A inhibitor is a CYP3A4 inhibitor and/or a CYP3A5 inhibitor. In a specific embodiment, the CYP3A inhibitor is a CYP3A4 inhibitor. In another specific embodiment, the CYP3A inhibitor is a CYP3A5 inhibitor. In yet another specific embodiment, the CYP3A inhibitor is a CYP3A7 inhibitor. In yet another specific embodiment, the CYP3A inhibitor is a CYP3A43 inhibitor.

While some drugs are deactivated by CYP3A4, there are also some drugs that are activated by the enzyme. In addition, the degree by which a drug is affected by CYP3A4 is usually unclear without investigation. Thus, even though it is known that CYP3A4 can be involved in drug metabolism, the effect of a modulator of CYP3A4 on a particular drug metabolism is not immediately predictable.

In some embodiments, the CYP3A inhibitor is a strong inhibitor of CYP3A. In other embodiments, the CYP3A inhibitor is a moderate inhibitor of CYP3A. In yet other embodiments, the CYP3A inhibitor is a weak inhibitor of CYP3A.

In some embodiments, the moderate inhibitor of CYP3A is selected from the group consisting of Aprepitant, Atazanavir, Atazanavir/Ritonavir, Ciprofloxacin, Darunavir, Darunavir/Ritonavir, Diltiazem, Dronedarone, Erythromycin, Fluconazole, Fosamprenavir, Grapefruit Juice, Imatinib, and Verapamil. In some embodiments, the moderate CYP3A inhibitor causes a 2- to 5-fold increase in systemic exposure (AUC) to a sensitive in vivo CYP3A probe substrate. In some embodiments, the moderate inhibitor of CYP3A increases the AUC of a substrate for CYP3A (e.g., pimavanserin) by equal or more than 2-fold. In some embodiments, the moderate inhibitor of CYP3A increases the AUC of a substrate for CYP3A (e.g., pimavanserin) by equal or more than 3-fold. In some embodiments, the moderate inhibitor of CYP3A increases the AUC of a substrate for CYP3A (e.g., pimavanserin) by equal or more than 4-fold. In some embodiments, the moderate inhibitor of CYP3A inhibits CYP3A4.

In some embodiments, the strong inhibitor of CYP3A is selected from the group consisting of Boceprevir, Clarithromycin, Cobicistat, Conivaptan, Indinavir, Itraconazole, Ketoconazole, Lopinavir/Ritonavir, Mibefradil, Nefazodone, Nelfinavir, Posaconazole, Ritonavir, Saquinavir, Telaprevir, Telithromycin, Troleandomycine and Voriconazole. In some embodiments, the strong inhibitor of CYP3A increases the AUC of a substrate for CYP3A (e.g., pimavanserin) by equal or more than 5-fold. In some embodiments, the strong inhibitor of CYP3A increases the AUC of a substrate for CYP3A (e.g., pimavanserin) by equal or more than 10-fold. In some embodiments, the strong inhibitor of CYP3A increases the AUC of a substrate for CYP3A (e.g., pimavanserin) by equal or more than 20-fold. In some embodiments, the strong inhibitor of CYP3A inhibits CYP3A4.

In certain embodiments, the patient having the disease or disorder to be treated with pimavanserin or a pharmaceutically acceptable salt thereof is on CYP modulator therapy to treat an infection. In some embodiments the infection is a fungal infection, a systemic infection, skin infection, toenail infection, fungal meningitis, blastomycosis, coccidioidomycosis, histoplasmosis, chromomycosis or paracoccidioidomycosis. In other embodiments, the infection treated by the CYP modulator is a bacterial infection. In yet other embodiments, the infection treated by the CYP modulator is a viral infection.

In yet other embodiments, the infection treated by the CYP modulator is a parasitic infection.

The methods provided herein can be used to treat or prevent a variety of human diseases or disorders in a patient on CYP modulator therapy.

The methods and the compositions provided herein can be used to treat various diseases or disorders treatable by pimavanserin or a pharmaceutically acceptable salt thereof, such as a neuropsychiatric disorder, a neurodegenerative disorder, and a condition induced by treatment of a neuropsychiatric or neurodegenerative disorder.

In some embodiments, the disease or disorder is a neurodegenerative disease selected from the group consisting of Parkinson's disease, Huntington's disease, Alzheimer's disease, Spinocerebellar Atrophy, Tourette's Syndrome, Friedrich's Ataxia, Machado-Joseph's disease, Lewy Body Dementia, Dystonia, Progressive Supranuclear Palsy, or Frontotemporal Dementia, or symptoms thereof. For example, in some specific embodiments, the disease or disorder is hallucinations or delusions associated with Parkinson's disease psychosis.

In yet other embodiments, the disease or disorder is a disease condition associated with a monoamine receptor. In some embodiments, the disease condition is selected from the group consisting of schizophrenia, psychosis, migraine, hypertension, thrombosis, vasospasm, ischemia, depression, anxiety, sleep disorders and appetite disorders. In some embodiments the disease condition is associated with dysfunction of a monoamine receptor. In some embodiments, the disease condition is associated with activation of a monoamine receptor. In some embodiments, the disease condition is associated with increased activity of monoamine receptor. In other embodiments, the disease condition is associated with improper function, dysfunction, or stimulation of native, as well as mutated or otherwise modified, forms of central or peripheral monoamine receptors. In one embodiment, the monamine receptor is serotonin receptor in the peripheral nervous system, blood or platelets. In some embodiments, the serotonin receptor is a 5-HT2A subclass receptor. In additional embodiments, the disease condition is associated with increased activity or activation of a serotonin receptor. In yet other embodiments, the disease condition arises from inappropriate stimulation or activation of serotonergic receptors. In yet other embodiments, the methods or compositions provided herein can be used for treating or alleviating symptoms of disease conditions associated with impaired function, in particular, elevated levels of activity, of especially 5-HT2A receptors, whether this impaired function is associated with improper levels of receptor stimulation or phenotypical aberrations.

In yet other embodiments, the disease or disorder is a neuropsyhiatric disease selected from the group consisting of schizophrenia, schizoaffective disorders, mania, behavioral disturbances associated with dementia and psychotic depression. In some embodiments, the disease or disorder is a neuropsychiatric disease such as schizophrenia and related idiopathic psychoses, anxiety, sleep disorders, appetite disorders, affective disorders such as major depression, bipolar disorder, and depression with psychotic features, and Tourette's Syndrome, drug-induced psychoses, psychoses secondary to neurodegenerative disorders such as Alzheimer's or Huntington's Disease. The neuropsychiatric diseases provided herein include schizophrenia, schizoaffective disorders, mania, behavioral disturbances associated with dementia and psychotic depression. For example, in some embodiments, the methods and compositions provided herein have utility in reducing the positive symptoms, improving negative symptoms and enhancing cognitive function in patients with certain neuropsychiatric diseases. In other embodiments, the methods and the compositions provided herein can improve psychotic symptoms (feelings of being controlled by outside forces, hearing, seeing, smelling or feeling things which are not there, hallucinations and unusual beliefs, delusions), negative symptoms (loss of normal behavior including tiredness, loss of concentration and lack of energy and motivation), and cognitive function in psychotic patients.

In one embodiment, the methods or compositions provided herein can be used to treat the negative symptoms of certain neuropsychiatric disease including schizophrenia as a monotherapy or as an adjunct to medicaments used to treat the positive symptom of these diseases.

In some embodiments, the methods or compositions provided herein can be used to improve cognitive function in certain neuropsychiatric disease including schizophrenia as a monotherapy or as an adjunct to medicaments used to treat the positive symptom of these diseases.

In yet other embodiments, the disease or disorder is selected from the group consisting of migraine, vasospasm, hypertension, various thrombotic conditions including myocardial infarction, thrombotic or ischemic stroke, idiopathic and thrombotic thrombocytopenic purpura, and peripheral vascular disease.

In one embodiment, the methods or compositions provided herein can be used to treat many side-effects that arise from antipsychotic therapy, such as motoric side-effects of other antipsychotic agents such as haloperidol.

In yet other embodiments, the disease or disorder is psychosis.

In some embodiments, the methods or compositions provided herein is for treating psychosis as a monotherapy or as an adjunct to medicaments to prevent or treat antipsychotic drug side-effects caused by the medicament. Alternatively, the methods or compositions provided herein may be given in combination with other compounds, which also reduce antipsychotic drug side-effects.

In some specific embodiments, the disease or disorder is Parkinson's disease psychosis. In other specific embodiments, the disease or disorder is Alzheimer's disease psychosis. In yet other specific embodiments, the disease or disorder is schizophrenia.

In a specific embodiment, the disease or disorder is Parkinson's disease psychosis and the CYP inhibitor is a CYP3A inhibitor such as a CYP3A4 inhibitor and/or a CYP3A5 inhibitor. In a specific embodiment, the disease or disorder is Alzheimer's disease psychosis and the CYP inhibitor is a CYP3A inhibitor such as a CYP3A4 inhibitor and/or a CYP3A5 inhibitor. In yet another specific embodiment, the disease or disorder is schizophrenia and the CYP inhibitor is a CYP3A inhibitor such as a CYP3A4 inhibitor and/or a CYP3A5 inhibitor.

In some embodiments, in addition to the above described diseases and disorders, the patient to be treated also has another condition that may be treated by a CYP modulator, e.g., a CYP3A inhibitor. For example, when ketoconazole is co-administered, the patient may have infections caused by fungus.

As shown in the Examples below, a patient's exposure to pimavanserin is altered by co-administration of a CYP modulator. Thus, the dose of pimavanserin can be (or should be recommended to be) changed in presence of a CYP modulator to maintain a similar exposure to pimavanserin to that when pimavanserin is administered in the absence of the CYP modulator.

In some embodiments, when a CYP3A inducer is co-administered, the dose of pimavanserin or pharmaceutical acceptable salt thereof is higher than a dose of pimavanserin or pharmaceutical acceptable salt thereof that would otherwise have been recommended to the patient if the patient were not currently taking the CYP3A inducer.

In some embodiments, when a CYP3A inducer is co-administered, the dose of pimavanserin or pharmaceutical acceptable salt thereof is more than 20% higher than a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 30% higher than a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 50% higher than a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 75% higher than a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 1.5-fold of a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 2-fold of a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 5-fold of a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 10-fold of a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 20-fold of a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 50-fold of a dose of pimavanserin or pharmaceutical acceptable salt thereof that would otherwise have been recommended to the patient if the patient were not currently taking the CYP3A inducer. In some embodiments, when a CYP3A inducer is co-administered, the dose of pimavanserin or pharmaceutical acceptable salt thereof is more than 100-fold of a dose of pimavanserin or pharmaceutical acceptable salt thereof that would otherwise have been recommended to the patient if the patient were not currently taking the CYP3A inducer.

In other embodiments, when a CYP3A inhibitor is co-administered, the dose of pimavanserin or a pharmaceutical acceptable salt thereof is lower than a dose of pimavanserin or a pharmaceutical acceptable salt thereof that would otherwise have been recommended to the patient if the patient were not currently taking the CYP3A inhibitor.

In other embodiments, when a CYP3A inhibitor, e.g., a CYP3A4 and/or CYP3A5 inhibitor, is co-administered, the dose of pimavanserin or a pharmaceutical acceptable salt thereof is about 10%-90% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor. In other embodiments, when a CYP3A inhibitor, e.g., a CYP3A4 and/or CYP3A5 inhibitor, is co-administered, the dose of pimavanserin or a pharmaceutical acceptable salt thereof is about 20%-80% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor. In other embodiments, when a CYP3A inhibitor, e.g., a CYP3A4 and/or CYP3A5 inhibitor, is co-administered, the dose of pimavanserin or a pharmaceutical acceptable salt thereof is about 30%-70% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor.

In other embodiments, when a CYP3A inhibitor, e.g., a CYP3A4 and/or CYP3A5 inhibitor, is co-administered, the dose of pimavanserin or a pharmaceutical acceptable salt thereof is about 10-20%, 15-35%, 20-30%, 25-35%, 30-40%, 40-50%, 50-60%, 65%-75%, or 70-80% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor In some embodiments, when a CYP3A inhibitor, e.g., a CYP3A4 and/or CYP3A5 inhibitor, is co-administered, the dose of pimavanserin or a pharmaceutical acceptable salt thereof is at least 20% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor. In some embodiments, when a CYP3A inhibitor, e.g., a CYP3A4 and/or CYP3A5 inhibitor, is co-administered, the dose of pimavanserin or a pharmaceutical acceptable salt thereof is at least 30% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor. In some embodiments, when a CYP3A inhibitor, e.g., a CYP3A4 and/or CYP3A5 inhibitor, is co-administered, the dose of pimavanserin or a pharmaceutical acceptable salt thereof is at least 40% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor. In some embodiments, when a CYP3A inhibitor, e.g., a CYP3A4 and/or CYP3A5 inhibitor, is co-administered, the dose of pimavanserin or a pharmaceutical acceptable salt thereof is at least 50% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor. In some embodiment, when a CYP3A inhibitor, e.g., a CYP3A4 and/or CYP3A5 inhibitor, is co-administered, the dose of pimavanserin or a pharmaceutical acceptable salt thereof is at least 60% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor. In some embodiments, when a CYP3A inhibitor, e.g., a CYP3A4 and/or CYP3A5 inhibitor, is co-administered, the dose of pimavanserin or a pharmaceutical acceptable salt thereof is at least 70% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor. In some embodiments, when a CYP3A inhibitor, e.g., a CYP3A4 and/or CYP3A5 inhibitor, is co-administered, the dose of pimavanserin or a pharmaceutical acceptable salt thereof is at least 80% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor.

In some embodiments, when a CYP3A inhibitor, e.g., a CYP3A4 and/or CYP3A5 inhibitor, is co-administered, the dose of pimavanserin or a pharmaceutical acceptable salt thereof is about 33% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor. In other embodiments, when a CYP3A inhibitor, e.g., a CYP3A4 and/or CYP3A5 inhibitor, is co-administered, the dose of pimavanserin or a pharmaceutical acceptable salt thereof is about 66% lower than a dose of pimavanserin or a pharmaceutical acceptable salt thereof that would otherwise have been recommended to the patient if the patient were not currently taking the CYP3A inhibitor, e.g., a CYP3A4 and/or CYP3A5 inhibitor.

In some embodiments, when a CYP3A inhibitor, e.g., a CYP3A4 and/or CYP3A5 inhibitor, is co-administered, pimavanserin or a pharmaceutical acceptable salt thereof is administered to the patient in a dose of 10-20, 15-25, 16-23, 20-30, 25-35, 35-45, 36-43, 40-50, 50-60, 60-70, 70-80, 75-85 mg.

In some embodiments, when a CYP3A inhibitor, e.g., a CYP3A4 and/or CYP3A5 inhibitor, is co-administered, pimavanserin (the compound of Formula (I)) in a dose of less than 27 mg is administered to the patient. In other embodiments, when a CYP3A inhibitor, e.g., a CYP3A4 and/or CYP3A5 inhibitor, is co-administered, pimavanserin in a dose of less than 23 mg is administered to the patient. In other embodiments, when a CYP3A inhibitor, e.g., a CYP3A4 and/or CYP3A5 inhibitor, is co-administered, pimavanserin in a dose of less than 15 mg is administered to the patient. In yet other embodiments, when a CYP3A inhibitor, e.g., a CYP3A4 and/or CYP3A5 inhibitor, is co-administered, pimavanserin in a dose of less than 12 mg is administered to the patient. In other embodiments, when a CYP3A inhibitor, e.g., a CYP3A4 and/or CYP3A5 inhibitor, is co-administered, pimavanserin in a dose of less than 10 mg is administered to the patient. In yet other embodiments, when a CYP3A inhibitor, e.g., a CYP3A4 and/or CYP3A5 inhibitor, is co-administered, pimavanserin in a dose of about 8.5-20 mg is administered to the patient. In yet other embodiments, when a CYP3A inhibitor, e.g., a CYP3A4 and/or CYP3A5 inhibitor, is co-administered, pimavanserin in a dose of about 12-19 mg is administered to the patient. In yet other embodiments, when a CYP3A inhibitor, e.g., a CYP3A4 and/or CYP3A5 inhibitor, is co-administered, pimavanserin in a dose of about 15-19 mg is administered to the patient. In a specific embodiment, when a CYP3A inhibitor, e.g., a CYP3A4 and/or CYP3A5 inhibitor, is co-administered, pimavanserin in a dose of about 17 mg is administered to the patient.

In some embodiments, a pharmaceutical salt of pimavanserin is administered to the patient. In some specific embodiments, a tartrate salt of pimavanserin is administered to the patient.

In some embodiments, when a CYP3A inhibitor, e.g., a CYP3A4 and/or CYP3A5 inhibitor, is co-administered, the tartrate salt of pimavanserin in a dose of less than 32 mg is administered to the patient. In some embodiments, when a CYP3A inhibitor, e.g., a CYP3A4 and/or CYP3A5 inhibitor, is co-administered, the tartrate salt of pimavanserin in a dose of less than 27 mg is administered to the patient. In some embodiments, when a CYP3A inhibitor, e.g., a CYP3A4 and/or CYP3A5 inhibitor, is co-administered, the tartrate salt of pimavanserin in a dose of less than 18 mg is administered to the patient. In some embodiments, when a CYP3A inhibitor, e.g., a CYP3A4 and/or CYP3A5 inhibitor, is co-administered, the tartrate salt of pimavanserin in a dose of less than 14 mg is administered to the patient. In some embodiments, when a CYP3A inhibitor, e.g., a CYP3A4 and/or CYP3A5 inhibitor, is co-administered, the tartrate salt of pimavanserin in a dose of less than 12 mg is administered to the patient.

In some embodiments, when a CYP3A inhibitor, e.g., a CYP3A4 and/or CYP3A5 inhibitor, is co-administered, the tartrate salt of pimavanserin in a dose of about 10-24 mg is administered to the patient. In a specific embodiment, when a CYP3A inhibitor, e.g., a CYP3A4 and/or CYP3A5 inhibitor, is co-administered, the tartrate salt of pimavanserin in a dose of about 20 mg (equivalent to 17 mg of free base pimavanserin) is administered to the patient.

In some embodiments, when a medium or strong inhibitor of CYP3A, such as a CYP3A4 inhibitor, is administered to a patient in need of a 5-HT2a inverse agonist such as pimavanserin or a pharmaceutically acceptable salt thereof (e.g., a tartrate salt), for example, to treat PDP or ADP, or one or more associated symptom(s), pimavanserin or a pharmaceutically acceptable salt thereof is administered at a reduced dose for at least half a day post-administering the medium or strong inhibitor of CYP3A, and thereafter the regular dose of pimavanserin or a pharmaceutically acceptable salt thereof is administered. In some embodiments, the reduced dose of pimavanserin is maintained for 1, 2, 3, 4, 5, 6, 7, 8, 9, 10, 11, 12, 13, 14, or 15 days post-administration of a medium or strong inhibitor of CYP3A. In other embodiments, a patient in need of a medium or strong inhibitor of CYP3A, such as a CYP3A4 inhibitor, and currently being administered with pimavanserin or a pharmaceutically acceptable salt thereof, is administered with a lower dose of pimavanserin before being administered the medium or strong inhibitor of CYP3A.

In other embodiments, when a CYP3A suppressor is co-administered, the dose of pimavanserin or a pharmaceutical acceptable salt thereof is lower than a dose of pimavanserin or a pharmaceutical acceptable salt thereof that would otherwise have been recommended to the patient if the patient were not currently taking the CYP3A suppressor.

In other embodiments, when a CYP3A suppressor, e.g., a CYP3A4 and/or CYP3A5 suppressor, is co-administered, the dose of pimavanserin or a pharmaceutical acceptable salt thereof is about 10%-90% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor. In other embodiments, when a CYP3A suppressor, e.g., a CYP3A4 and/or CYP3A5 suppressor, is co-administered, the dose of pimavanserin or a pharmaceutical acceptable salt thereof is about 20%-80% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor. In other embodiments, when a CYP3A suppressor, e.g., a CYP3A4 and/or CYP3A5 suppressor, is co-administered, the dose of pimavanserin or a pharmaceutical acceptable salt thereof is about 30%-70% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor.

In other embodiments, when a CYP3A suppressor, e.g., a CYP3A4 and/or CYP3A5 suppressor, is co-administered, the dose of pimavanserin or a pharmaceutical acceptable salt thereof is about 10-20%, 15-35%, 20-30%, 25-35%, 30-40%, 40-50%, 50-60%, 65%-75%, or 70-80% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor In some embodiments, when a CYP3A suppressor, e.g., a CYP3A4 and/or CYP3A5 suppressor, is co-administered, the dose of pimavanserin or a pharmaceutical acceptable salt thereof is at least 20% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor. In some embodiments, when a CYP3A suppressor, e.g., a CYP3A4 and/or CYP3A5 suppressor, is co-administered, the dose of pimavanserin or a pharmaceutical acceptable salt thereof is at least 30% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor. In some embodiments, when a CYP3A suppressor, e.g., a CYP3A4 and/or CYP3A5 suppressor, is co-administered, the dose of pimavanserin or a pharmaceutical acceptable salt thereof is at least 40% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor. In some embodiments, when a CYP3A suppressor, e.g., a CYP3A4 and/or CYP3A5 suppressor, is co-administered, the dose of pimavanserin or a pharmaceutical acceptable salt thereof is at least 50% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor. In some embodiment, when a CYP3A suppressor, e.g., a CYP3A4 and/or CYP3A5 suppressor, is co-administered, the dose of pimavanserin or a pharmaceutical acceptable salt thereof is at least 60% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor. In some embodiments, when a CYP3A suppressor, e.g., a CYP3A4 and/or CYP3A5 suppressor, is co-administered, the dose of pimavanserin or a pharmaceutical acceptable salt thereof is at least 70% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor. In some embodiments, when a CYP3A suppressor, e.g., a CYP3A4 and/or CYP3A5 suppressor, is co-administered, the dose of pimavanserin or a pharmaceutical acceptable salt thereof is at least 80% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor.

In some embodiments, when a CYP3A suppressor, e.g., a CYP3A4 and/or CYP3A5 suppressor, is co-administered, the dose of pimavanserin or a pharmaceutical acceptable salt thereof is about 33% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor. In other embodiments, when a CYP3A suppressor, e.g., a CYP3A4 and/or CYP3A5 suppressor, is co-administered, the dose of pimavanserin or a pharmaceutical acceptable salt thereof is about 66% lower than a dose of pimavanserin or a pharmaceutical acceptable salt thereof that would otherwise have been recommended to the patient if the patient were not currently taking the CYP3A suppressor, e.g., a CYP3A4 and/or CYP3A5 suppressor.

In some embodiments, when a CYP3A suppressor, e.g., a CYP3A4 and/or CYP3A5 suppressor, is co-administered, pimavanserin or a pharmaceutical acceptable salt thereof is administered to the patient in a dose of 10-20, 15-25, 16-23, 20-30, 25-35, 35-45, 36-43, 40-50, 50-60, 60-70, 70-80, 75-85 mg.

In some embodiments, when a CYP3A suppressor, e.g., a CYP3A4 and/or CYP3A5 suppressor, is co-administered, pimavanserin (the compound of Formula (I)) in a dose of less than 27 mg is administered to the patient. In other embodiments, when a CYP3A suppressor, e.g., a CYP3A4 and/or CYP3A5 suppressor, is co-administered, pimavanserin in a dose of less than 23 mg is administered to the patient. In yet other embodiments, when a CYP3A suppressor, e.g., a CYP3A4 and/or CYP3A5 suppressor, is co-administered, pimavanserin in a dose of less than 12 mg is administered to the patient. In yet other embodiments, when a CYP3A suppressor, e.g., a CYP3A4 and/or CYP3A5 suppressor, is co-administered, pimavanserin in a dose of about 8.5-20 mg is administered to the patient. In yet other embodiments, when a CYP3A suppressor, e.g., a CYP3A4 and/or CYP3A5 suppressor, is co-administered, pimavanserin in a dose of about 12-19 mg is administered to the patient. In yet other embodiments, when a CYP3A suppressor, e.g., a CYP3A4 and/or CYP3A5 suppressor, is co-administered, pimavanserin in a dose of about 15-19 mg is administered to the patient. In a specific embodiment, when a CYP3A suppressor, e.g., a CYP3A4 and/or CYP3A5 suppressor, is co-administered, pimavanserin in a dose of about 17 mg is administered to the patient.

The exact route of administration, dose, or frequency of administration would be readily determined by those skilled in the art and can be dependent on the age, weight, general physical condition, or other clinical symptoms specific to the patient to be treated.

In some embodiments, the tartrate salt of pimavanserin is administered daily. In some embodiments, the tartrate salt of pimavanserin is administered once daily. In some embodiments, the tartrate salt of pimavanserin is formulated for oral administration as a unit dose. In a specific embodiment, the unit dose is a tablet.

As used in the context of the present invention, the term "co-administration" refers to the administration of both pimavanserin or a pharmaceutical acceptable salt thereof, and the CYP modulator within the same dosing period. In some embodiments, a dosing period is less than 24 hours. In some embodiments, a dosing period is 1, 2, 3, 4, 5, 6, or 7 days, more than 1 week, or more than two weeks.

EXAMPLES

Example 1—Evaluation of Pharmacokinetics, Safety and Tolerability of Administration of Pimavanserin in Presence of a CYP3A Inhibitor The effect of multiple doses of ketoconazole (a strong CYP3A inhibitor) on the pharmacokinetics of pimavanserin was evaluated in this exemplary study. The safety and tolerability of single-dose of pimavanserin alone and in the presence of ketoconazole were also evaluated.

Subjects 20 subjects (14 males and 6 females) were enrolled in this study. These subjects were healthy male or female subjects between the ages of 18 and 55 years, and with a body mass index (BMI) between 18 and 30 kg/m$^2$. Among the 20 subjects, 10 subjects (50%) were black, 9 subjects (45%) were white and 1 subject (5%) was American Indian/Alaska native. 19 subjects completed the study, one subject was discontinued from the study due to an adverse event (AE)-elevated blood creatinine level, and no other subjects withdrew from the study for any reason. The subject who was discontinued was not replaced.

Drug Administration

On Day 1, subjects received a single oral dose of pimavanserin tartrate 40 mg (2×20 mg tablets) under fasting conditions. On Day 15, subjects began taking ketoconazole 400 mg (2×200 mg tablets) orally once daily for 14 days. A single oral dose of pimavanserin tartrate 40 mg was administered under fasting conditions 60 minutes after the fifth ketoconazole dose (on Day 19). Both single doses of pimavanserin tartrate were administered on an empty stomach, following an overnight fast of approximately 10 hours prior to dosing. Subjects continued to fast for 4 hours after administration of pimavanserin tartrate.

Screening procedures to determine subject eligibility were performed within approximately 4 weeks of the first dose of study drug administration on Day 1. Eligible subjects reported to the Clinical Pharmacology Unit (CPU) at study check-in (evening of Day −1) and were required to stay in the CPU for approximately 3 days until the morning of Day 3. Subjects returned to the clinic for outpatient visits on Days 4, 5, 7, 9, 12, 15, 16, 17, and 18. Subjects were admitted to the CPU once again from Days 18 to 23, and after discharge on Day 23, returned to the clinic for outpatient visits on Study Days 24, 25, 26, 27, 28, 30, and 33. After the last treatment visit on Day 33, subjects returned to the CPU 5 to 9 days later to complete all end of study assessments.

Determination of Pimavanserin Pharmacokinetics

Samples for pimavanserin pharmacokinetic (PK) analysis were collected prior to each pimavanserin dose and at scheduled time points up to 14 days post-dose. More specifically, blood samples for the determination of plasma pimavanserin and four of its metabolites were collected at the following time points in relation to pimavanserin dosing on Day 1 and Day 19: pre-dose (within 30 minutes of dosing), 1, 2, 4, 6, 9, 12, 16, 24, 36, 48, 72, 96, 144, 192, 264, and 336 hours post-dose. The pharmacokinetics of pimavanserin and four metabolites, M1 (N-desmethyl-pimavanserin), M2 (O-desalkyl-pimavanserin), M3 ([ω-1]-hydroxy-pimavanserin), and M4 (ω-hydroxy-pimavanserin), by treatment consisting of pimavanserin alone and pimavanserin with ketoconazole, were assessed using noncompartmental analysis.

The following parameters were determined for pimavanserin, M1, M2 and M3 (the analytes for which there was a sufficient number of quantifiable post-dose concentrations): the area under the concentration-time curve from 0 to the time of the last measurable concentration ($AUC_{0-t}$); the area from 0 to infinity ($AUC_{0-inf}$); the percent of the extrapolated portion of the $AUC_{0-inf}$ (% $AUC_{ext}$); the maximum observed plasma concentration ($C_{max}$); time of maximum plasma concentration ($T_{max}$); apparent first-order terminal elimination rate constant ($k_{el}$), and apparent first-order terminal elimination half-life ($t_{1/2}$). Additional PK parameters computed for pimavanserin were oral clearance (CL/F), and apparent volume of distribution ($V_z$/F). Where feasible, as in the case of pimavanserin, M1, M2 and M3, parent ratios, which were computed as AUC(metabolite)/AUC(parent) ratios based on both $AUC_{0-t}$ and $AUC_{0-inf}$ were also determined.

Determination of Safety and Tolerability

Safety data (including adverse events (AEs)), laboratory tests, vital sign measurements, electrocardiograms (ECGs), and physical examination (PE) were reviewed throughout the study for the purpose of safety monitoring. Clinical laboratory assessments were obtained on Day −1, Day 18, and the end of study visit. Vital signs were performed at each study visit, except on Day −1. A 12-lead ECG was performed on Day −1, Day 1, Day 19 and the end of study visit. Other safety measures included physical examination on Days −1, 3, 23, and the end of study visit and any other measures deemed necessary.

Statistical Methods

A two-sided paired t-test was performed on the natural log-transformed pimavanserin $AUC_{0-t}$, $AUC_{0-inf}$, and $C_{max}$ at the alpha level of 0.05. The geometric ratio of treatment means (pimavanserin with ketoconazole/pimavanserin alone) and 90% geometric confidence intervals for the ratio of means were calculated for $AUC_{0-t}$, $AUC_{0-inf}$, and $C_{max}$.

As ketoconazole was expected to influence the pharmacokinetics of pimavanserin in a significant manner, the study was not powered to meet bioequivalence criteria (90% CIs between 80 and 125%). Thus, a sample size of 16 completed subjects was considered adequate to assess the impact of ketoconazole on pimavanserin pharmacokinetics.

All available safety data from subjects receiving at least one dose of study medication were included in the safety analyses. The frequency of AEs was tabulated. Pre-treatment, within study, and end of study, and change from pre-treatment laboratory, vital signs, and ECG parameters were summarized. Shift tables were prepared for laboratory parameters.

Results 20 subjects received pimavanserin and ketoconazole and were included in the population for assessing safety and tolerability, and 19 subjects fully completed the drug-interaction phase (pimavanserin with ketoconazole) of the study and were included in the population for assessing PK.

As shown in Table 1 below, ketoconazole co-administration resulted in higher pimavanserin exposure compared with that for administration of pimavanserin alone.

TABLE 1

Pimavanserin Exposure for Co-administration of Ketoconazole and Pimavanserin and Administration of Pimavanserin Alone

| Parameter (unit) | Pimavanserin Alone | Pimavanserin with Ketoconazole | Ratio of Mean Exposures (Pimavanserin with Ketoconazole/ Pimavanserin alone) |
|---|---|---|---|
| $AUC_{0-t}$ (ng · h/mL) | 1224 ± 433 | 3415 ± 768 | 2.8 |
| $AUC_{0-inf}$ (ng · h/mL) | 1257 ± 464 | 3783 ± 912 | 3.0 |
| $C_{max}$ (ng/mL) | 17.1 ± 3.8 | 25.1 ± 5.5 | 1.5 |

The ratio of the geometric means for both pimavanserin $AUC_{0-inf}$ and $AUC_{0-t}$ was approximately 3 for pimavanserin concomitantly administered with ketoconazole relative to pimavanserin administered alone. An increase of approximately 1.5-fold in pimavanserin Cmax was observed following ketoconazole co-administration.

The rank order of metabolite exposure in humans in decreasing order was M1>M2>M3>M4 (which was undetectable). Ketoconazole co-administration resulted in a net (26%) increase in mean M1 $AUC_{0-t}$ relative to administration of pimavanserin alone. Without being bound to any theory, the increase of M1 $AUC_{0-t}$ may be due to that ketoconazole inhibits the clearance of M1 more than its formation. Only 5 of the 19 subjects had a few measurable plasma levels of M3. With ketoconazole administration, plasma concentrations of M3 were not detectable in any subjects. Ketoconazole co-administration with pimavanserin resulted in decreased plasma concentrations of M2, with undetectable concentrations in most subjects. Without being bound to any theory, it is possible that CYP3A is involved in the (ω-1)-hydroxylation and O-dealkylation of pimavanserin to M3 and M2, respectively.

No deaths or serious adverse events occurred during the study. A total of 13 (65%) subjects had a total of 22 treatment emergent adverse events (TEAEs) during the study. All TEAEs were considered mild in severity and all but one had resolved by the end of the study. 1 subject had an adverse event of amphetamine-positive urine on Day 39 that had not resolved at the end of study. 10 (50%) subjects had a total of 16 treatment-related TEAEs during the study. 8 (50%) of the 16 treatment-related TEAEs were considered related to pimavanserin and 12 (75%) of the 16 treatment-related TEAEs were considered related to ketoconazole. Treatment-related TEAEs considered related to pimavanserin included headache, dizziness, dyspepsia, abdominal distension, fatigue, and nausea. Treatment-related TEAEs considered related to ketoconazole included eye pain, headache, rash, elevated blood creatinine, and diarrhea. The most common treatment-related TEAE reported was headache. 7 (43.75%) of the treatment-related TEAEs were adverse events of headache. The reported treatment-related TEAEs were clinically consistent with known pharmacologic effects of both pimavanserin and ketoconazole. Other TEAEs reported, but not considered treatment-related, included eye irritation, vomiting, presyncope, amphetamine-positive urine, headache, and dizziness.

No trends or clinically relevant changes were noted in mean clinical laboratory, vital signs, 12-lead ECG, or physical examination findings following administration of pimavanserin alone or pimavanserin administered with ketoconazole.

In sum, this study shows that co-administration of multiple doses of ketoconazole 400 mg daily with a single 40 mg dose of pimavanserin tartrate resulted in a 3-fold increase in pimavanserin AUC and a 1.5-fold increase in pimavanserin Cmax.

After a single dose of pimavanserin, exposure to pimavanserin metabolites, as assessed by mean AUC ratios, was highest for the N-desmethyl metabolite M1 (1.47), followed by O-desalkyl metabolite M2 (0.0365). Low levels of M3 ([ω-1]-hydroxy-pimavanserin) were observed in only 5 subjects, and there were no detectable concentrations of M4 (w-hydroxy-pimavanserin) in any subjects. Co-administration of ketoconazole with pimavanserin may inhibit the clearance of M1, as well as its formation. M2 and M3 levels were reduced when ketoconazole was present, consistent with inhibition of metabolism of pimavanserin by CYP3A.

Pimavanserin administered alone and pimavanserin administered with ketoconazole were safe and generally well tolerated in healthy adult subjects.

Example 2—In Vitro Study of the Role for a CYP3A4 Inhibitor in Pimavanserin Metabolism Pimavanserin is extensively metabolized, predominantly in the liver. Pimavanserin undergoes multiple sequential metabolic steps to form hydrophilic metabolites that can be efficiently eliminated in urine or bile.

A major metabolite formed in vitro by human liver microsomes, M1 (N-desmethyl-pimavanserin), was identified as a significant circulating metabolite in humans in vivo. M1 has similar receptor activity to pimavanserin. The elimination half-life of M1 is about 65 hours. In vitro studies established that the primary metabolites of pimavanserin are formed predominantly by the cytochrome P450 (CYP) 3A4 enzymes with a minor role for CYP2J2, an enzyme whose substrates are also substrates of CYP3A4, along with contributions from numerous other CYP and flavin monooxygenase enzymes.

An in vitro study was performed to analyze the role of a CYP3A4 inhibitor in pimavanserin metabolism.

Pharmacokinetic simulations were performed to study the impact of strong inhibition of CYP3A4 on the steady-state $C_{max}$ of pimavanserin. These simulations demonstrated that pimavanserin $C_{max}$ after a 34 mg once-daily dose would increase 2.9-fold, from 73 to 209 ng/mL. If administration of a strong CYP3A4 inhibitor were countered with a simultaneous 50% reduction in dose (from 34 mg/day to 17 mg/day), $C_{max}$ would increase about 1.4-fold, from 73 ng/mL to 104 ng/mL. Therefore, a 50% dose reduction can be recommended when pimavanserin is coadministered with moderate to strong inhibitors of CYP3A4.

The in vitro data demonstrating a major role for CYP3A4 in pimavanserin metabolism are consistent with the data shown in Example 1 above.

Example 3—Effects of Pimavanserin on the Pharmacokinetic of Midazolam and its Metabolites In this study, the pharmacokinetics of midazolam, a sensitive in vivo probe drug for CYP3A4 and an accepted probe drug for CYP3A4, were evaluated in the presence of pimavanserin in humans. The results showed that pimavanserin has no immediate or delayed effect on midazolam exposure (no induction or inhibition of CYP3A4) following dosing with 34 mg pimavanserin for up to 38 days. No dose adjustment is therefore required for other CYP3A4 substrates when coadministered with pimavanserin.

While this specification contains many specifics, these should not be construed as limitations on the scope or of what may be claimed, but rather as descriptions of features specific to particular embodiments. Certain features that are described in this specification in the context or separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

All publications and patent applications cited in this specification are herein incorporated by reference as if each individual publication or patent application were specifically and individually indicated to be incorporated by reference. Although the foregoing has been described in some detail by way of illustration and example for purposes of clarity of understanding, it will be readily apparent to those of ordinary skill in the art in light of the teachings of the specification that certain changes and modifications may be made thereto without departing from the spirit or scope of the appended claims.

The invention claimed is:

1. A method of treating psychosis secondary to neurodegenerative disorders in a patient in need thereof, wherein the patient is being treated concurrently with a strong CYP3A4 inhibitor selected from the group consisting of: ketoconazole, clarithromycin, indinavir, and itraconazole, comprising orally administering to the patient 10 mg of pimavanserin or a pharmaceutically acceptable salt thereof once daily.

2. The method of claim 1, wherein the 10 mg of pimavanserin is a unit dose comprising pimavanserin tartrate.

3. The method of claim 1, wherein the psychosis is Parkinson's disease psychosis or Alzheimer's disease psychosis.

4. The method of claim 1, wherein the strong CYP3A4 inhibitor is ketoconazole.

5. A method of treating hallucinations and delusions associated with Parkinson's disease in a patient in need thereof, wherein the patient is being treated concurrently with ketoconazole, comprising orally administering to the patient 10 mg of pimavanserin once daily.

* * * * *